United States Patent
Iizuka et al.

(10) Patent No.: US 10,005,856 B2
(45) Date of Patent: Jun. 26, 2018

(54) CURABLE COMPOSITION

(71) Applicant: FUJIFILM Corporation, Tokyo (JP)

(72) Inventors: Yuusuke Iizuka, Ashigarakami-gun (JP); Satoshi Sano, Ashigarakami-gun (JP); Keisuke Kodama, Ashigarakami-gun (JP); Sotaro Inomata, Ashigarakami-gun (JP); Kuniyuki Kaminaga, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days. days.

(21) Appl. No.: 15/430,941

(22) Filed: Feb. 13, 2017

(65) Prior Publication Data

US 2017/0152331 A1 Jun. 1, 2017

Related U.S. Application Data

(63) Continuation of application No. PCT/JP2015/070808, filed on Jul. 22, 2015.

(30) Foreign Application Priority Data

Aug. 28, 2014 (JP) .................... 2014-173958

(51) Int. Cl.
C08F 22/38 (2006.01)
B01J 39/20 (2006.01)
(Continued)

(52) U.S. Cl.
CPC ............ C08F 22/38 (2013.01); B01D 53/228 (2013.01); B01D 61/002 (2013.01);
(Continued)

(58) Field of Classification Search
CPC ......... C08F 22/38; B01D 61/02; B01D 61/42; B01D 61/00; B01D 61/46; B01D 71/40;
(Continued)

(56) References Cited

U.S. PATENT DOCUMENTS 9,193,817 B2 * 11/2015 Iizuka .................. C08F 220/30
9,393,181 B2 * 7/2016 Bock .................... A61K 6/0023
(Continued)

FOREIGN PATENT DOCUMENTS

GB 1371160 A 10/1974
JP 2005-514338 A 5/2005
(Continued)

OTHER PUBLICATIONS

International Search Report (PCT/ISA/210) issued in PCT/JP2015/070808, dated Sep. 29, 2015.
(Continued)

*Primary Examiner* — Michael M Bernshteyn
(74) *Attorney, Agent, or Firm* — Birch, Stewart, Kolasch & Birch, LLP

(57) ABSTRACT

Provided are a curable composition including an amide compound that is represented by Formula (1) below and of which a density of sulfonic acid is 3.9 milliequivalent/g or greater.

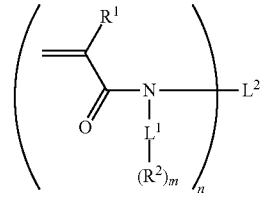

Formula (1)

m represents an integer of 1 or greater, n represents an integer of 2 or greater, $L^1$ represents a m+1-valent linking group, and $L^2$ represents an n-valent linking group. $R^1$ represents a hydrogen atom or an alkyl
(Continued)

group, and $R^2$ represents $-SO_3^-M^+$ or $-SO_3R^3$ ($R^3$ represents an alkyl group or an aryl group). Here, in a case where there are plural $R^2$'s, not all of the $R^2$'s are $-SO_3R^3$. $M^+$ represents a hydrogen ion, an inorganic ion, or an organic ion.

8 Claims, 1 Drawing Sheet

(51) Int. Cl.
| | |
|---|---|
| *B01J 47/12* | (2017.01) |
| *B01D 61/46* | (2006.01) |
| *B01D 71/40* | (2006.01) |
| *C07C 309/15* | (2006.01) |
| *C07C 309/51* | (2006.01) |
| *B01D 53/22* | (2006.01) |
| *B01D 61/00* | (2006.01) |
| *B01D 61/02* | (2006.01) |
| *B01D 61/42* | (2006.01) |
| *C07C 303/32* | (2006.01) |

(52) U.S. Cl.
CPC ......... *B01D 61/025* (2013.01); *B01D 61/422* (2013.01); *B01D 61/46* (2013.01); *B01D 71/40* (2013.01); *B01J 39/20* (2013.01); *B01J 47/12* (2013.01); *C07C 303/32* (2013.01); *C07C 309/15* (2013.01); *C07C 309/51* (2013.01)

(58) Field of Classification Search
CPC ..... B01D 53/22; C07C 309/51; C07C 309/15; C07C 303/32; B01J 47/12; B01J 39/20
USPC ......................................................... 521/27
See application file for complete search history.

(56) References Cited

U.S. PATENT DOCUMENTS

2004/0266906 A1    12/2004  Klee et al.
2013/0090404 A1*   4/2013   Bock .................... A61K 6/0023
                                                             522/28

FOREIGN PATENT DOCUMENTS

JP        2009-079338 A       4/2009
WO        WO 2013/011272 A1   1/2013

OTHER PUBLICATIONS

Written Opinion (PCT/ISA/237) issued in PCT/JP2015/070808, dated Sep. 29, 2015.
Extended European Search Report dated May 4, 2017, for corresponding European Application No. 15836038.8.
International Preliminary Report on Patentability and English translation of Written Opinion of the International Searching Authority issued in PCT/JP2015/070808, dated Feb. 28, 2017 (Forms PCT/IB/373 and PCT/ISA/237).
European Communication Pursuant to Article 94(3) EPC dated Feb. 23, 2018 for corresponding European Application No. 15836038.8.

* cited by examiner

CURABLE COMPOSITION

CROSS-REFERENCE TO RELATED APPLICATIONS

This application is a Continuation of PCT International Application No. PCT/JP2015/070808 filed on Jul. 22, 2015, which claims priority under 35 U.S.C. § 119 (a) to Japanese Patent Application No. 2014-173958 filed on Aug. 28, 2014. Each of the above applications is hereby expressly incorporated by reference, in its entirety, into the present application.

BACKGROUND OF THE INVENTION

1. Field of the Invention

The present invention relates to a curable composition, a functional polymer hardened product, a stack or a device comprising a functional polymer membrane, an amide compound, and a manufacturing method thereof.

2. Description of the Related Art

Among functional polymer membranes, the ion-exchange membrane is used in electrodeionization (EDI), continuous electrodeionization (CEDI), electrodialysis (ED), electrodialysis reversal (EDR), and reverse electrodialysis (RED). Recently the ion-exchange membrane has also been used in a solid polymer electrolyte-type fuel cell.

The electrodeionization (EDI) is a water treatment process for removing ions from aqueous liquids by using an ion-exchange membrane and a potential in order to achieve ion transport. Differently from other water purification technologies, such as conventional ion exchange, the electrodeionization (EDI) does not require the use of chemicals such as acids or caustic soda, and can be used to produce ultra pure water. The electrodialysis (ED) and the electrodialysis reversal (EDR) are electrochemical separation processes for removing ions and the like from water and other fluids.

As a main raw material of an ion-exchange membrane, an acrylamide-based polymer is generally used. This acrylamide-based polymer can be manufactured at a low cost by using a photopolymerizable monomer such as acrylamide by an ultraviolet (UV) hardening process.

The acrylamide-based polymer can be used not only for an ion-exchange membrane but also for various uses. Therefore, research has been actively conducted. For example, JP2005-514338A discloses an acrylamide-based polymer that is used for a dental adhesive composition and that has a phosphonic acid moiety or a sulfonic acid moiety.

Recently, research for improvement on a membrane that has crosslinking with an ionic group with a high density by using a monomer (also referred to as a charged crosslinker or an ionic crosslinking agent) combined with two or more polymerizable groups (crosslinking groups) that can perform crosslinking reaction with ionic groups has been actively conducted, and a cation-exchange membrane having an anionic group such as a sulfo group is suggested (for example, WO2013/011272A).

SUMMARY OF THE INVENTION

It is ideal that a functional polymer membrane (hereinafter, simply referred to as a "membrane") such as an ion-exchange membrane is basically required to have high ion permselectivity (hereinafter, simply referred to as "permselectivity"). In a practical point of view and in view of realizing this, it is required that both of electrical resistance and hydraulic permeability are low and, additionally, durability is excellent. However, required levels thereof become higher, year by year.

Particularly, according to reviews of the present inventors, a membrane surface of a membrane in the related art was observed with a scanning electron microscope (SEM) to find that pin holes are generated. With respect to the durability, it was found that, in addition to pH resistance in the related art, it is required to improve the stability of the membrane by preventing deterioration of characteristics of the membrane, particularly, mass reduction, against vibration such as ultrasonic waves.

In addition to this, with respect to the functional polymer membrane such as a cation-exchange membrane in which a sulfo group is used in an ion exchange group, differently from using an onio group such as quaternary ammonium in an ion exchange group, in view of synthesis, only limited charged crosslinkers having sulfo groups are known. Therefore, it is considered that it is possible to further improve performances of the functional polymer membrane by improving a charged crosslinker having a sulfo group.

Accordingly, an object of the invention is to provide a curable composition including a charged crosslinker having a sulfo group, that is suitably used in manufacturing of a functional polymer membrane of which permselectivity is excellent, both of hydraulic permeability and electrical resistance are low, pin holes are not generated, and stability to pH or vibration and durability are excellent. Another object of the invention is to provide a functional polymer hardened product obtained by hardening this curable composition, a stack or a device comprising a functional polymer membrane, an amide compound that can cause a functional polymer membrane to have characteristics described above, and a manufacturing method thereof.

Though it is important that both of electrical resistance and hydraulic permeability of a membrane are reduced, in a case where the reduction is difficult, the present inventors had a target of reducing a product of the electrical resistance and the hydraulic permeability and conducted research for various charged crosslinkers having sulfo groups.

As a result, with respect to the durability, the present inventors found that, in a case where a polymerizable group had a hydrogen atom on a nitrogen atom of an amido group of a (meth)acrylamido group having higher durability than a (meth)acryloyl group, durability is deteriorated. The present inventors synthesized various charged crosslinkers having different density of sulfo groups, that is, sulfonic acid and conducted research. As a result, the present inventors found that a specific amide compound having a high density of sulfonic acid is effective for achieving the objects of the invention described above to conceive the invention.

The above objects are achieved by the following means.

<1> A curable composition comprising: an amide compound that is represented by Formula (1) below and of which a density of sulfonic acid is 3.9 milliequivalent/g or greater.

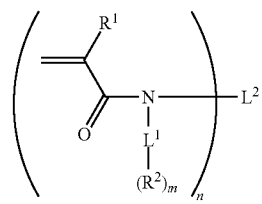

Formula (1)

In Formula (1), m represents an integer of 1 or greater; n represents an integer of 2 or greater; $L^1$ represents a m+1-valent linking group; $L^2$ represents an n-valent linking group; $R^1$ represents a hydrogen atom or an alkyl group; $R^2$ represents $-SO_3^-M^+$ or $-SO_3R^3$; here, in a case where there are plural $R^2$'s, not all of the $R^2$'s are $-SO_3R^3$; $M^+$ represents a hydrogen ion, an inorganic ion, or an organic ion; and $R^3$ represents an alkyl group or an aryl group.

<2> The curable composition according to <1>, that is used for forming a functional polymer membrane.

<3> The curable composition according to <1> or <2>, that is used for forming an ion-exchange membrane.

<4> The curable composition according to any one of <1> to <3>, in which the amide compound is an amide compound represented by Formula (2) below.

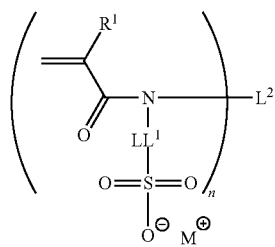

Formula (2)

In Formula (2), $LL^1$ represents an alkylene group; and n, $R^1$, $L^2$, and $M^+$ respectively have the same meanings as n, $R^1$, $L^2$, and $M^+$ in Formula (1).

<5> The curable composition according to any one of <1> to <3>, in which the amide compound is an amide compound represented by Formula (3) below.

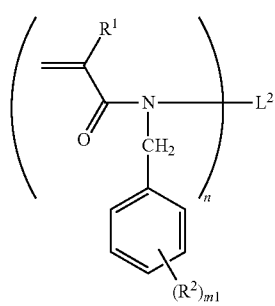

Formula (3)

In Formula (3), m1 represents an integer of 1 to 5; and n, $R^1$, $R^2$, and $L^2$ respectively have the same meanings as n, $R^1$, $R^2$, and $L^2$ in Formula (1).

<6> The curable composition according to any one of <1> to <5>, in which a molecular weight of the amide compound is 900 or less.

<7> The curable composition according to any one of <1> to <6>, further comprising: a polymerization initiator.

<8> The curable composition according to any one of <1> to <7>, further comprising: a solvent.

<9> A functional polymer hardened product obtained by performing polymerization hardening reaction on the curable composition according to any one of <1> to <8>.

<10> The functional polymer hardened product according to <9>, which is a functional polymer membrane.

<11> The functional polymer hardened product according to <10>, which is an ion-exchange membrane.

<12> A stack, comprising: the functional polymer hardened product according to any one of <9> to <11>.

<13> A device, comprising: the functional polymer hardened product according to any one of <9> to <11>.

<14> A manufacturing method of an amide compound, comprising: manufacturing a compound represented by Formula (2) below from a compound represented by Formula (4) below.

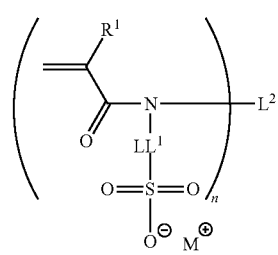

Formula (2)

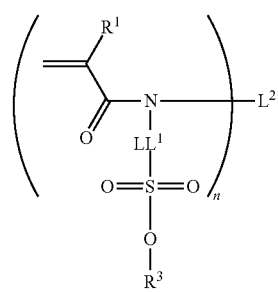

Formula (4)

In Formulae (2) and (4), n represents an integer of 2 or greater; $LL^1$ represents an alkylene group; $L^2$ represents an n-valent linking group; $R^1$ represents a hydrogen atom or an alkyl group; $M^+$ represents a hydrogen ion, an inorganic ion, or an organic ion; and $R^3$ represents an alkyl group or an aryl group.

<15> A manufacturing method of an amide compound, comprising: manufacturing the compound represented by Formula (4) according to <14> from a compound represented by Formula (5) below.

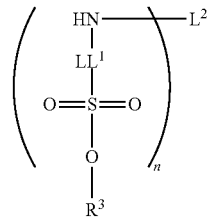

Formula (5)

In Formula (5), n, $R^3$, $LL^1$, and $L^2$ respectively have the same meanings as n, $R^3$, $LL^1$, and $L^2$ in Formula (4).

<16> A compound represented by Formula (6) below, in which a density of sulfonic acid is 3.9 milliequivalent/g or greater.

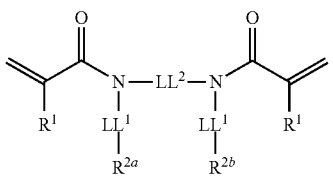

Formula (6)

In Formula (6), $LL^1$ represents an alkylene group; $LL^2$ represents an alkylene group; $R^1$ represents a hydrogen atom or an alkyl group; $R^{2a}$ and $R^{2b}$ each independently represent $-SO_3^-M^+$ or $-SO_3R^3$; here, not both of $R^{2a}$ and $R^{2b}$ are $-SO_3R^3$; $M^+$ represents a hydrogen ion, an inorganic ion, or an organic ion; and $R^3$ represents an alkyl group or an aryl group.

<17> A compound represented by Formula (7) below.

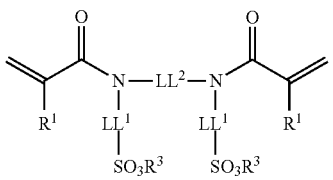

Formula (7)

In Formula (7), $LL^1$ represents an alkylene group; $LL^2$ represents an alkylene group; represents a hydrogen atom or an alkyl group; and $R^3$ represents an alkyl group or an aryl group.

In this specification, the expression "to" is used to have a meaning of including numerical values indicated before and after the expression "to" as a lower limit and an upper limit.

In this specification, unless described otherwise, in respective formulae, in a case where there are plural groups indicated by the same reference numerals, these groups may be identical to or different from each other. In the same manner, in a case where there are plural repetitions of partial structures, the repetitions mean both of the identical repetitions or mixture of different repetitions in a regulated scope.

Further, unless otherwise described, a geometric isomer which is a substitution form of a double bond in respective formulae may be an E isomer or a Z isomer, or a mixture thereof, even if one type of an isomer is described, for convenience of indication.

Unless described otherwise, in a case where a group is simply described as a "substituent", the group refers to a substituent of a substituent group α, and means this substituent.

According to the invention, the expression "(meth)acryl" includes a group in which not only a methyl group but also an alkyl group are substituted at an α position of an acyl group such as acryl or methacryl, and used as an expression collectively referring to acids thereof, salts thereof, esters thereof, or amides thereof. That is, both of an acrylic acid ester, amide, or acid, or salts thereof and an α-alkyl substituted acrylic acid ester, amide, or acid or salts thereof are included.

According to the invention, it is possible to provide a curable composition including a charged crosslinker having a sulfo group, that is suitably used in manufacturing of a functional polymer membrane of which permselectivity is excellent, both of hydraulic permeability and electrical resistance are low, pin holes are not generated, and stability to pH or vibration and durability are excellent. According the invention, it is possible to provide a functional polymer hardened product obtained by hardening this curable composition, a stack or a device comprising a functional polymer membrane, an amide compound that can cause a functional polymer membrane to have performances described above, and a manufacturing method thereof.

Aforementioned and other characteristics and advantages of the invention can be revealed by the following description appropriately with reference to the accompanying drawings.

DESCRIPTION OF THE PREFERRED EMBODIMENTS

<<Curable Composition>>

Figure 1:
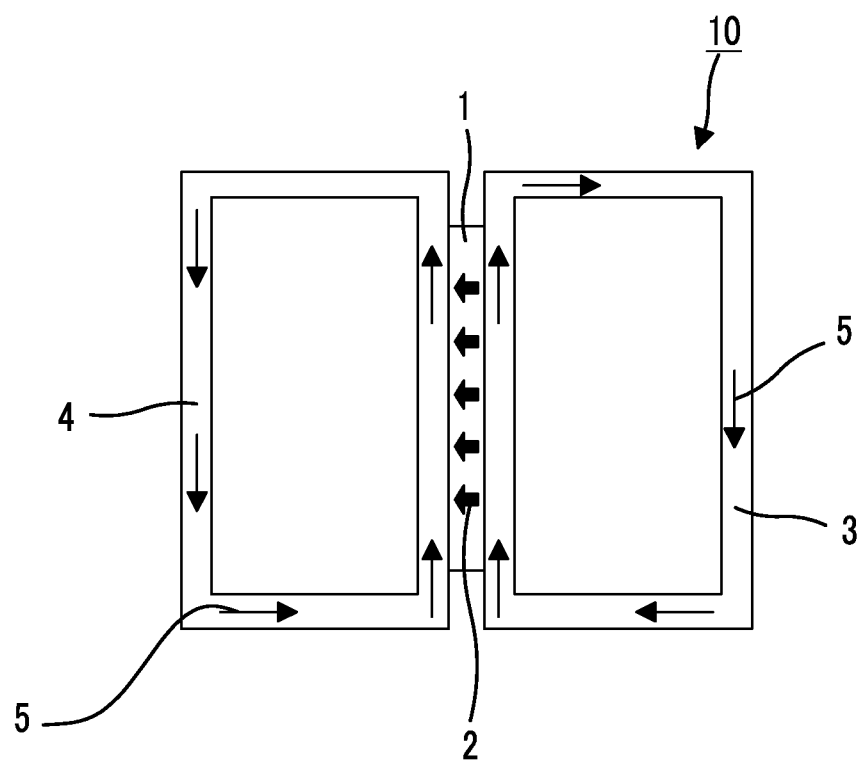
FIG. 1 is a diagram schematically illustrating a flow channel of a device for measuring hydraulic permeability of a membrane.

The curable composition according to the invention includes an amide compound (hereinafter, referred to as an amide compound according to the invention) that is represented by Formula (1) and of which a density of sulfonic acid is 3.9 milliequivalent/g or greater. Since the amide compound represented by Formula (1) has at least two ethylenically unsaturated bonds as polymerizable groups, crosslinking polymerization becomes possible.

According to the invention, the polymerizable group is a group that is polymerized by active radiation such as ultraviolet rays or heating, and examples thereof include an ethylenically unsaturated group, an epoxy group, and an oxetanyl group. An ethylenically unsaturated group does not represent a double bond such as a benzene ring but represents a vinyl group (also including a styryl group), an allyl group, and a group such as $-Z-C(=O)C(R^{1a})=CH_2$. Here, $R^{1a}$ represents a hydrogen atom or an alkyl group, Z represents $-O-$ or $-N(R^Z)-$, and $R^Z$ represents a hydrogen atom or a substituent.

In addition to the amide compound according to the invention, the curable composition according to the invention may contain a compound having a chemical structure different from the amide compound according to the invention that has two or more polymerizable groups or a compound having one polymerizable group, and also preferably contains a polymerization initiator, a polymerization inhibitor, and a solvent.

In addition to the above, the curable composition according to the invention may include a chain transfer agent, a surfactant, a polymer dispersant, a viscosity improver, a surface tension adjuster, a preservative, and an anti-crater agent.

<Amide Compound According to the Invention>

In the amide compound according to the invention, a density of sulfonic acid is 3.9 milliequivalent/g or greater.

[Density of Sulfonic Acid]

The density of sulfonic acid is an equivalent of sulfonic acid groups in 1 g of the compound, and if there are A items of sulfonic acid groups are included in one molecule having a molecular weight M, the density is A/M equivalent /g.

The fact that the density of sulfonic acid of the amide compound according to the invention is 3.9 milliequivalent/g or greater means that a molecular weight per one sulfonic acid group in one molecule is small, and indicates that sulfonic acid densely exists.

The density of sulfonic acid of the amide compound according to the invention is preferably 4.0 milliequivalent/g or greater and more preferably 4.5 milliequivalent/g or greater. The upper limit of the density of sulfonic acid is practically 6.5 milliequivalent/g or less and preferably 6.0 milliequivalent/g or less.

If the density of sulfonic acid of the amide compound according to the invention is 3.9 milliequivalent/g or greater, ion (cation) exchange capacity increases such that electrical resistance of the membrane can be suppressed.

The density of sulfonic acid can be obtained as described in examples.

Generally, if the density of sulfonic acid increases, there is a concern that hydraulic permeability increases, since a sulfonic acid group is hydrophilic. However, a membrane that is obtained by polymerizing and hardening the curable composition according to the invention has a high crosslink density as well as a high density of sulfonic acid, and thus it is possible to suppress both of the electrical resistance and the hydraulic permeability of the membrane.

Since the amide compound according to the invention has a specific structure represented by Formula (1), if the curable composition according to the invention is polymerized and hardened, distribution of the sulfonic acid group in the membrane is not deviated but is even in a high density and thus it is possible to suppress the generation of pin holes together with suppressing electrical resistance.

[Molecular Weight]

The molecular weight of the amide compound according to the invention is preferably 900 or less, more preferably 800 or less, and particularly preferably 600 or less. The lower limit of the molecular weight is not particularly limited, but the lower limit is generally 400 or greater.

If the molecular weight is 900 or less, the density of sulfonic acid of the amide compound according to the invention can be caused to be in the range described above.

The amide compound according to the invention is an amide compound represented by Formula (1) below. Since the amide compound has two or more polymerizable groups (n below is 2 or greater), the amide compound performs crosslinking polymerization, is called a so-called crosslinking agent, and can allow crosslinking of a three-dimensional network.

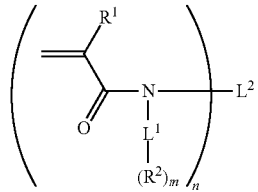

Formula (1)

In Formula (1), m represents an integer of 1 or greater. n represents an integer of 2 or greater. $L^1$ represents an m+1-valent linking group. $L^2$ represents an n-valent linking group. $R^1$ represents a hydrogen atom or an alkyl group. $R^2$ represents $-SO_3^-M^+$ or $-SO_3R^3$. Here, in a case where there are plural $R^2$'s, not all of $R^2$'s are $-SO_3R^3$. $M^+$ represents a hydrogen ion, an inorganic ion, or an organic ion. $R^3$ represents an alkyl group or an aryl group.

m preferably represents an integer of 1 to 5 and more preferably represents 1 or 2.

n preferably represents an integer of 2 to 5, more preferably represents 2 or 3, and particularly preferably represents 2. $L^2$ preferably represents a divalent to pentavalent linking group, this divalent to pentavalent linking group has the same meaning as a divalent to pentavalent linking group in $L^1$ described below, and preferable ranges thereof are the same.

The alkyl group in $R^1$ is a linear or branched alkyl group. The number of carbon atoms is preferably 1 to 10, more preferably 1 to 5, even more preferably 1 to 3, and particularly preferably 1. Specific examples of the alkyl group include methyl, ethyl, isopropyl, t-butyl, n-octyl, 2-ethylhexyl, and n-decyl.

$R^1$ preferably represents a hydrogen atom or methyl and more preferably represents a hydrogen atom.

The alkyl group in $R^1$ may have an arbitrary substituent.

The inorganic ion in $M^+$ is preferably an alkali metal ion. Examples of the alkali metal ion preferably include a lithium ion, a potassium ion, and a sodium ion.

Examples of the organic ion in $M^+$ include an ammonium ion, a quaternary ammonium ion, a pyridinium ion, an imidazolium ion, and a morpholium ion.

$M^+$ preferably represents a hydrogen ion and an inorganic ion, more preferably represents a hydrogen ion, a lithium ion, a potassium ion, and a sodium ion, and particularly preferably a sodium ion.

The alkyl group in $R^3$ is a linear or branched alkyl group. The number of carbon atoms is preferably 1 to 10, more preferably 1 to 5, and particularly preferably 3. Specific examples of the alkyl group include methyl, ethyl, isopropyl, t-butyl, n-octyl, 2-ethylhexyl, and n-decyl.

An alkyl group in $R^3$ may have a substituent.

In the aryl group in $R^3$, the number of carbon atoms is preferably 6 to 12, more preferably 6 to 10, and even more preferably 6 to 8. The aryl group may have a substituent. The aryl group is preferably phenyl.

The divalent linking group in $L^1$ is preferably an alkylene group or an arylene group. In addition to this, a group obtained by combining groups selected from an alkylene group, a cycloalkylene group, an arylene group, a divalent heterocyclic group, $-O-$, $-S-$, $-SO-$, $-SO_2-$, $-C(=O)-$, and $-N(Ra)-$ is also preferable. Here, Ra represents a hydrogen atom, an alkyl group, or an aryl group. Ra described below is also the same.

The alkylene group is a linear or a branched alkylene group, the number of carbon atoms is preferably 1 to 10, more preferably 1 to 8, even more preferably 1 to 6, particularly preferably 2 to 5, and most preferably 2. The alkylene group may have a substituent.

The number of carbon atoms of the arylene group is preferably 6 to 12, more preferably 6 to 8, and particularly preferably 6. The arylene group may have a substituent.

The number of combinations in the group obtained by combining groups selected from an alkylene group, a cycloalkylene group, an arylene group, a divalent heterocyclic group, $-O-$, $-S-$, $-SO-$, $-SO_2-$, $-C(=O)-$, and $-N(Ra)-$ is preferably 2 to 8, more preferably 2 to 6, even more preferably 2 to 4, and particularly preferably 2 or 3.

Examples of the combined group include an alkylene-arylene group, an alkylene-arylene-alkylene group, an alkylene-cycloalkylene-alkylene group, an alkylene-O-alkylene group, an alkylene-S-alkylene group, an alkylene-SO-alkylene group, an alkylene-SO$_2$-alkylene group, an alkylene-N(Ra)-alkylene group, an alkylene-C(=O)-alkylene group, an alkylene-C(=O)—N(Ra)-alkylene group, an alkylene-O-arylene-O-alkylene group, an alkylene-O-arylene-O- alkylene group, an alkylene-S-arylene-S-alkylene group, and an alkylene-O-arylene-alkylene-arylene-O-alkylene group.

Here, an alkylene group in "alkylene" preferably has 1 to 10 carbon atoms, as in methylene, ethylene, ethylidene, 2,2-propylene, propylidene, and isopropylidene, more preferably has 1 to 4 carbon atoms, even more preferably has 1 or 2 carbon atoms, and particularly preferably has 1 carbon atom.

A cycloalkylene group in "cycloalkylene" is preferably a 5-membered or 6-membered ring, more preferably cyclopentylene and cyclohexylene, and even more preferably 1,3-cyclohexylene.

Meanwhile, an arylene group in "arylene" is preferably a phenylene group, and 1,3-phenylene is preferable. A linking group obtained by combining these groups may have a substituent.

As a trivalent linking group, a trivalent alkyl group or a trivalent aryl group is preferable. In addition to this, a group obtained by combining groups selected from a trivalent alkyl group, a trivalent aryl group, a trivalent heterocyclic group, —O—, —S—, —SO—, —SO$_2$—, —C(=O)—, and >N—, —N(Ra)— is also preferable.

As a tetravalent linking group, a tetravalent alkyl group or a tetravalent aryl group is preferable. In addition to this, a group obtained by combining groups selected from a tetravalent alkyl group, a tetravalent aryl group, a tetravalent heterocyclic group, —O—, —S—, —SO—, —SO$_2$—, —C(=O)—, >N—, and —N(Ra)— is also preferable.

As a pentavalent linking group, a pentavalent alkyl group or a pentavalent aryl group is preferable. In addition to this, a group obtained by combining groups selected from a pentavalent alkyl group, a pentavalent aryl group, a pentavalent heterocyclic group, —O—, —S—, —SO—, —SO$_2$—, —C(=O)—, >N—, and —N(Ra)— is also preferable.

L$^1$ preferably represents a divalent or trivalent linking group. Among the divalent or trivalent linking groups, an alkylene group, an alkylene-divalent or a trivalent phenylene group is preferable. Meanwhile, L$^2$ is preferably a divalent linking group, and an alkylene group, an alkylene-phenylene-alkylene group, and an alkylene-cycloalkylene-alkylene group are preferable.

According to the invention, the amide compound represented by Formula (1) is preferably an amide compound represented by any one of Formula (2) and (3) below.

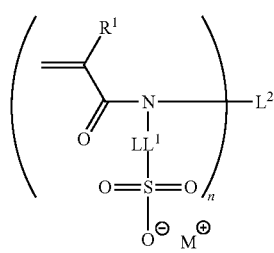

Formula (2)

In Formula (2), LL$^1$ represents an alkylene group. n, R$^1$, L$^2$, and M$^+$ respectively have the same meanings as n, R$^1$, L$^2$, and M$^+$ Formula (1), and preferable ranges thereof are also the same.

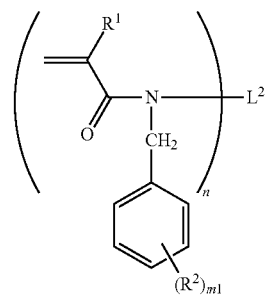

Formula (3)

In Formula (3), m1 represents an integer of 1 to 5. n, R$^1$, R$^2$, and L$^2$ respectively have the same meanings as n, R$^2$, and L$^2$ in Formula (1), and preferable ranges thereof are also the same.

According to the invention, the amide compound represented by Formula (1) is represented by Formula (6) below, and a compound of which a density of sulfonic acid is 3.9 milliequivalent/g or greater is preferable.

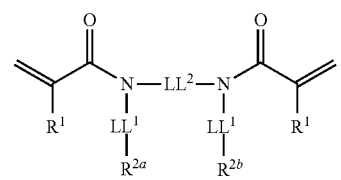

Formula (6)

In Formula (6), LL$^1$ represents an alkylene group. LL$^2$ represents an alkylene group. R$^1$ represents a hydrogen atom or an alkyl group. R$^{2a}$ and R$^{2b}$ each independently represent —SO$_3^-$M$^+$ or —SO$_3$R$^3$. Here, not both of R$^{2a}$ and R$^{2b}$ are —SO$_3$R$^3$. M$^+$ represents a hydrogen ion, an inorganic ion, or an organic ion. R$^3$ represents an alkyl group or an aryl group.

Here, R$^1$ has the same meaning as R$^1$ in Formula (1), R$^{2a}$ and R$^{2b}$ have the same meaning as R$^2$ in Formula (1), and respectively preferable ranges thereof are also the same. LL$^1$ and LL$^2$ have the same meaning as LL$^1$ in Formula (2), and preferable ranges thereof are also the same.

Examples of the substituent represent a group selected from the substituent group α below.

[Substituent Group α]

Examples of the substituent group α may include an alkyl group (an alkyl group preferably having 1 to 30 carbon atoms, more preferably having 1 to 20 carbon atoms, and particularly preferably having 1 to 10 carbon atoms, and examples thereof include methyl, ethyl, i-propyl, t-butyl, n-octyl, 2-ethylhexyl, n-decyl, and n-hexadecyl), a cycloalkyl group (a cycloalkyl group preferably having 3 to 30 carbon atoms, more preferably having 3 to 20 carbon atoms, and particularly preferably having 3 to 10 carbon atoms, and examples thereof include cyclopropyl, cyclopentyl, and cyclohexyl), an alkenyl group (an alkenyl group preferably having 2 to 30 carbon atoms, more preferably having 2 to 20 carbon atoms, and particularly preferably having 2 to 10 carbon atoms, and examples thereof include vinyl, allyl, 2-butenyl, and 3-pentenyl), an alkynyl group (an alkynyl group preferably having 2 to 30 carbon atoms, more preferably having 2 to 20 carbon atoms, and particularly preferably having 2 to 10 carbon atoms, and examples thereof include propargyl and 3-pentynyl), an aryl group (an aryl group preferably having 6 to 30 carbon atoms, more preferably having 6 to 20 carbon atoms, particularly preferably having 6 to 12 carbon atoms, and examples thereof include phenyl, p-methylphenyl, naphthyl, and anthranyl), an amino group (an amino group includes an amino group, an alkylamino group, and an arylamino group, the amino group is an amino group preferably having 0 to 30 carbon atoms, more preferably having 0 to 20 carbon atoms, and particularly preferably having 0 to 10 carbon atoms, and examples thereof include amino, methylamino, dimethylamino, diethylamino, dibenzylamino, diphenylamino, and ditolylamino), an alkoxy group (an alkoxy group preferably having 1 to 30 carbon atoms, more preferably having 1 to 20 carbon atoms, particularly preferably having 1 to 10 carbon atoms, and examples thereof include methoxy, ethoxy, butoxy, and 2-ethylhexyloxy), an aryloxy group (an aryloxy group preferably having 6 to 30 carbon atoms, more preferably having 6 to 20 carbon atoms, and particularly preferably having 6 to 12 carbon atoms, and examples thereof include phenyloxy, 1-naphthyloxy, and 2-naphthyloxy), and a heterocyclic oxy group (a heterocyclic oxy group preferably having 2 to 30 carbon atoms, more preferably having 2 to 20 carbon atoms, particularly preferably having 2 to 12 carbon atoms, and examples thereof include pyridyloxy, pyrazyloxy, and pyrimidyloxy, and quinolyloxy).

Examples of the substituent group α may include an acyl group (an acyl group preferably having 1 to 30 carbon atoms, more preferably having 1 to 20 carbon atoms, and particularly preferably having 1 to 12 carbon atoms, and examples thereof include acetyl, benzoyl, formyl, and pivaloyl), an alkoxycarbonyl group (an alkoxycarbonyl group preferably having 2 to 30 carbon atoms, more preferably having 2 to 20 carbon atoms, and particularly preferably having 2 to 12 carbon atoms, and examples thereof include methoxycarbonyl and ethoxycarbonyl), an aryloxycarbonyl group (an aryloxycarbonyl group preferably having 7 to 30 carbon atoms, more preferably having 7 to 20 carbon atoms, and particularly preferably having 7 to 12 carbon atoms, and examples thereof include phenyloxycarbonyl), an acyloxy group (an acyloxy group preferably having 2 to 30 carbon atoms, more preferably having 2 to 20 carbon atoms, and particularly preferably having 2 to 10 carbon atoms, and examples thereof include acetoxy and benzoyloxy), and an acylamino group (an acylamino group preferably having 2 to 30 carbon atoms, more preferably having 2 to 20 carbon atoms, and particularly preferably having 2 to 10 carbon atoms, and examples thereof include acetylamino and benzoylamino).

Examples of the substituent group α may include an alkoxycarbonylamino group (an alkoxycarbonylamino group preferably having 2 to 30 carbon atoms, more preferably having 2 to 20 carbon atoms, and particularly preferably having 2 to 12 carbon atoms, and examples thereof include methoxycarbonylamino), an aryloxycarbonylamino group (an aryloxycarbonylamino group preferably having 7 to 30 carbon atoms, more preferably having 7 to 20 carbon atoms, particularly preferably having 7 to 12 carbon atoms, and examples thereof include phenyloxycarbonylamino), an alkyl or aryl sulfonylamino group (preferably having 1 to 30 carbon atoms, more preferably having 1 to 20 carbon atoms, and particularly preferably having 1 to 12 carbon atoms, and examples thereof include methanesulfonylamino and benzenesulfonylamino), and a sulfamoyl group (the sulfamoyl group includes a sulfamoyl group, and an alkyl or aryl sulfamoyl group, the sulfamoyl group is a sulfamoyl group preferably having 0 to 30 carbon atoms, more preferably having 0 to 20 carbon atoms, and particularly preferably having 0 to 12 carbon atoms, and examples thereof include sulfamoyl, methylsulfamoyl, dimethylsulfamoyl, and phenylsulfamoyl).

Examples of the substituent group α may include a carbamoyl group (the carbamoyl group includes a carbamoyl group, an alkyl or aryl carbamoyl group, the carbamoyl group is a carbamoyl group preferably having 1 to 30 carbon atoms, more preferably having 1 to 20 carbon atoms, and particularly preferably having 1 to 12 carbon atoms, and examples thereof include carbamoyl, methylcarbamoyl, diethylcarbamoyl, and phenylcarbamoyl), an alkylthio group (an alkylthio group preferably having 1 to 30 carbon atoms, more preferably having 1 to 20 carbon atoms, and particularly preferably having 1 to 12 carbon atoms, and examples thereof include methylthio, and ethylthio), an arylthio group (an arylthio group preferably having 6 to 30 carbon atoms, more preferably having 6 to 20 carbon atoms, and particularly preferably having 6 to 12 carbon atoms, and examples thereof include phenylthio), and a heterocyclic thio group (a heterocyclic thio group preferably having 2 to 30 carbon atoms, more preferably having 2 to 20 carbon atoms, and particularly preferably having 2 to 12 carbon atoms, and examples thereof include pyridylthio, 2-benzimidazolylthio, 2-benzoxazolylthio, and 2-benzothiazolylthio).

Examples of the substituent group α may include an alkyl or aryl sulfonyl group (an alkyl or aryl sulfonyl group preferably having 1 to 30 carbon atoms, more preferably having 1 to 20 carbon atoms, and particularly preferably having 1 to 12 carbon atoms, and examples thereof include mesyl and tosyl), an alkyl or aryl sulfinyl group (an alkyl or aryl sulfinyl group preferably having 1 to 30 carbon atoms, more preferably having 1 to 20 carbon atoms, and particularly preferably having 1 to 12 carbon atoms, and examples thereof include methanesulfinyl, and benzenesulfinyl), an ureido group (an ureido group preferably having 1 to 30 carbon atoms, more preferably having 1 to 20 carbon atoms, particularly preferably having 1 to 12 carbon atoms, and examples thereof include ureido, methylureido, and phenylureido), a phosphoric acid amide group (a phosphoric acid amide group preferably having 1 to 30 carbon atoms, more preferably having 1 to 20 carbon atoms, particularly preferably having 1 to 12 carbon atoms, and examples thereof include diethyl phosphoric acid amide and phenyl phosphoric acid amide), a hydroxyl group, a mercapto group, and a halogen atom (for example, a fluorine atom, a chlorine atom, a bromine atom, and an iodine atom, and a fluorine atom is more preferable).

Examples of the substituent group α may include a cyano group, a sulfo group, a carboxy group, an oxo group, a nitro group, a hydroxamic acid group, a sulfino group, a hydrazino group, an imino group, and a heterocyclic group (a heterocyclic group preferably having 1 to 30 carbon atoms and more preferably having 1 to 12 carbon atoms, as a ring-constituting hetero atom, for example, a nitrogen atom, an oxygen atom, and a sulfur atom are preferable, and specific examples thereof include imidazolyl, pyridyl, quinolyl, furyl, thienyl, piperidyl, morpholino, benzoxazolyl, benzimidazolyl, benzothiazolyl, a carbazolyl group, and an azepinyl group), a silyl group (a silyl group preferably having 3 to 40 carbon atoms, more preferably having 3 to 30 carbon atoms, and particularly preferably having 3 to 24 carbon atoms, and examples thereof include trimethylsilyl and triphenylsilyl), and a silyloxy group (a silyloxy group preferably having 3 to 40 carbon atoms, more preferably having 3 to 30 carbon atoms, particularly preferably having 3 to 24 carbon atoms, and examples thereof include trimethylsilyloxy and triphenylsilyloxy). These substituents may be further substituted with any one or more substituents selected from the substituent group α above.

According to the invention, when there are plural substituents in one structural portion, the substituents may be linked to each other to form a ring or may be condensed with a portion or all of the structural portion to form an aromatic ring or an unsaturated heterocyclic ring.

Specific examples of the amide compound represented by Formula (1) are provided below, but the invention is not limited thereto.

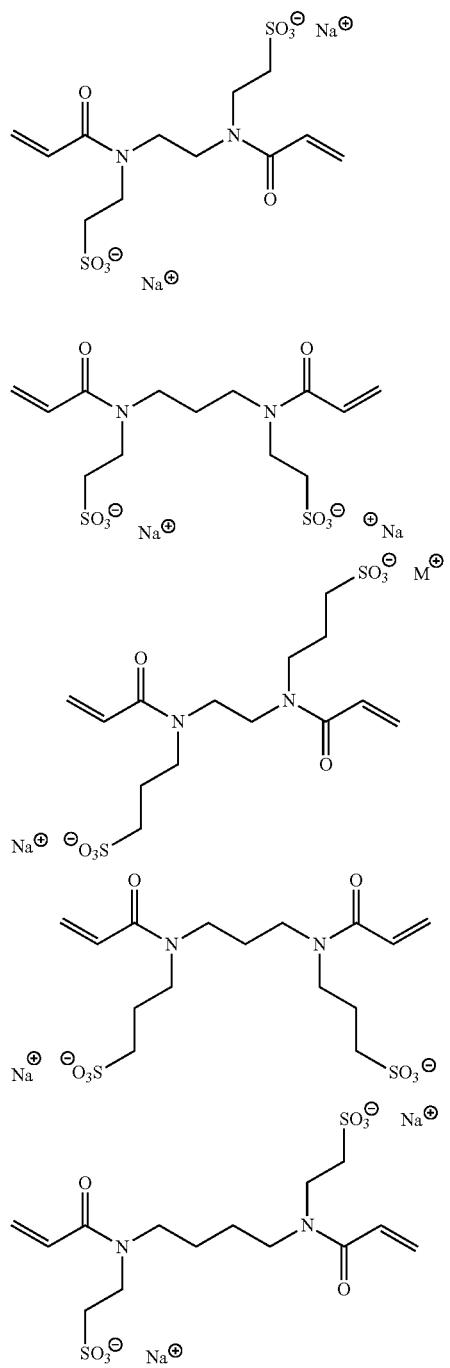

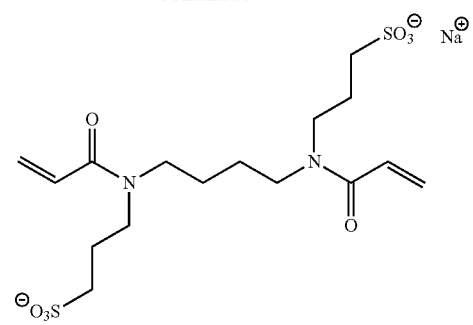

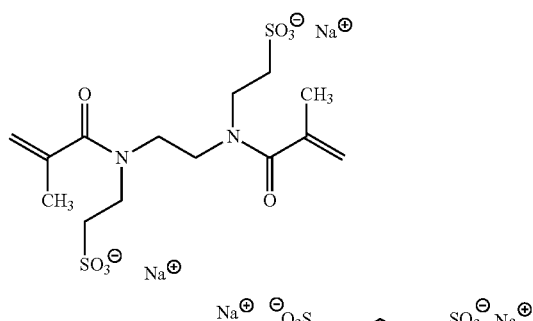

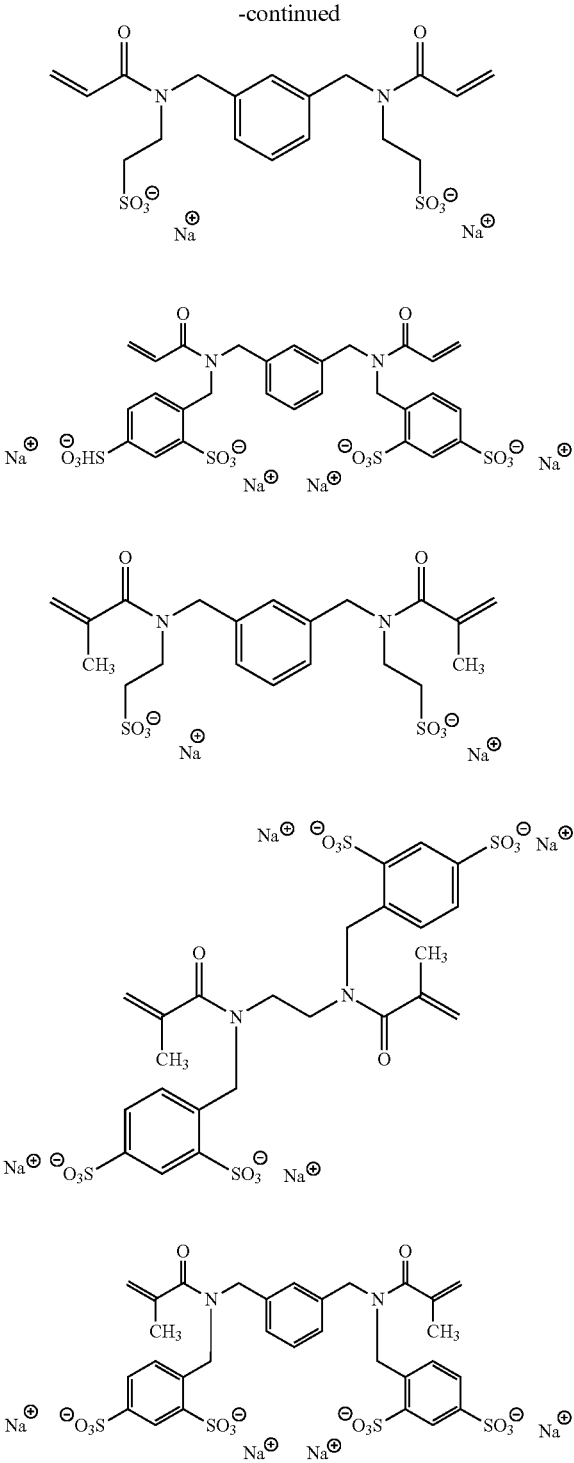

<Manufacturing Method of Amide Compound According to Invention>

The manufacturing method of the amide compound represented by Formula (1) is described with reference to the manufacturing method of the amide compound represented by Formula (2).

The amide compound represented by Formula (2) is preferably manufactured by using a compound represented by Formula (4) below as a synthesized raw material.

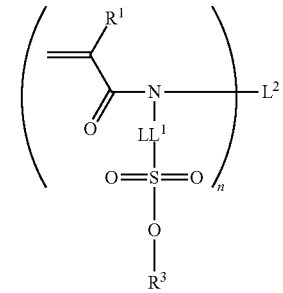

Formula (4)

In Formula (4), $L^2$, $R^1$, and $R^3$ respectively have the same meanings as $L^2$, $R^1$, and $R^3$ in Formula (1), and preferable ranges thereof are also the same. $LL^1$ has the same meaning as $LL^1$ in Formula (2), and a preferable range thereof is also the same.

Here, as the compound represented by Formula (4), a compound represented by Formula (7) below is preferable among the compounds.

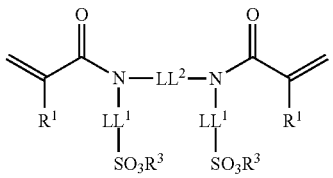

Formula (7)

In Formula (7), $LL^1$ represents an alkylene group. $LL^2$ represents an alkylene group. $R^1$ represents a hydrogen atom or an alkyl group. $R^3$ represents an alkyl group or an aryl group.

$R^1$, $LL^1$, and $R^3$ have the same meanings as $R^1$, $LL^1$, and $R^3$ in Formula (4), and preferable ranges thereof are also the same. $LL^2$ has the same meaning as $LL^2$ in Formula (6), and preferable ranges thereof are also the same.

The amide compound represented by Formula (2) can be manufactured by processing the compound represented by Formula (4) as below.

The amide compound represented by Formula (2) is manufactured by cleaving an O—$R^3$ bond of the amide compound represented by Formula (4).

The cleavage condition may be an acid condition or a base condition, but is preferably an acid condition.

Examples of the acid include hydrochloric acid, phosphoric acid, acetic acid, benzenesulfonic acid, p-toluenesulfonic acid, methanesulfonic acid, and sulfuric acid. Among these, p-toluenesulfonic acid, methanesulfonic acid, and sulfuric acid are preferable, and sulfuric acid is more preferable.

Examples of the base include sodium hydroxide and potassium hydroxide. Among these, sodium hydroxide is preferable.

As the reaction solvent, water and a water soluble solvent are preferable. A water soluble solvent is a solvent that is not hydrolyzed or decomposed in an acid or base condition, and an alcohol solvent, a nitrile solvent, and a ketone solvent are preferable.

Specifically, as the reaction solvent, water, methanol, ethanol, isopropanol, acetonitrile, acetone, and the like are preferable, and it is possible to use these in a mixture. The reaction solvent is preferably a mixture solvent of water and a solvent selected from methanol, ethanol, isopropanol, acetonitrile, and acetone.

As an reaction temperature, a temperature in which reaction sufficiently proceeds, and polymerization of acrylamide that may have an alkyl group at an a position does not proceed is appropriate. The reaction temperature is preferably 0° C. to 100° C., more preferably 20° C. to 80° C., and particularly preferably 40° C. to 60° C.

Here, the compound represented by Formula (4) is preferably manufactured by using the compound represented by Formula (5) below as a synthesized raw material.

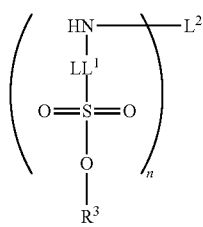

Formula (5)

In Formula (5), n, $R^3$, $LL^1$, and $L^2$ has the same meaning as n, $R^3$, $LL^1$, and $L^2$ in Formula (4), and preferable ranges thereof are also the same.

Particularly, it is preferable to cause the compound represented by Formula (5) and a compound represented by Formula (a) below to react with each other.

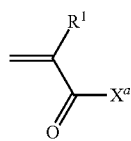

Formula (a)

In Formula (a), $R^1$ has the same meaning as $R^1$ in Formula (1), and a preferable range is also the same. $X^a$ represents a halogen atom, an alkoxy group, an aryloxy group, an acyloxy group, an alkylsulfonyloxy group, an arylsulfonyloxy group, or a hydroxyl group.

$X^a$ preferably represents a halogen atom. Among halogen atoms, a chlorine atom is preferable.

A compound represented by Formula (4) can be manufactured by reacting the compound represented by Formula (5) and the compound represented by Formula (a) in presence of base.

As a reaction solvent used in this reaction, a halogenated hydrocarbon solvent, a nitrile solvent, an ether solvent (cyclic ether-containing solvent), and an amide solvent are preferable. Specific examples thereof include dichloromethane, chloroform, acetonitrile, tetrahydrofuran, dioxane, and dimethyl acetamide. Dichloromethane, acetonitrile, and tetrahydrofuran are preferable.

Examples of the base include organic or inorganic base. As an organic salt group, alkylamine (tertiary amine is preferable), a heterocyclic amine (5-membered or 6-membered amine, for example, pyrrolidine, piperazine, and pyridine compounds) are preferable, and as an inorganic salt group, carbonate or hydrogen carbonate is preferable.

Specifically preferable examples of base include triethylamine, diisopropylethylamine, pyridine, dimethylaminopyridine, potassium carbonate, and sodium hydrogen carbonate, and triethylamine, diisopropylethylamine, and pyridine are more preferable.

As the reaction temperature, temperature at which reaction sufficiently proceeds, and polymerization of acrylamide that may have an alkyl group at an a position does not proceed is appropriate. The reaction temperature is preferably −10° C. to 100° C., more preferably 0° C. to 60° C., and particularly preferably 0° C. to 25° C.

<Compound Having Polymerizable Group Other than Amide Compound According to Invention>

According to the invention, in addition to an amide compound according to the invention, a compound having a polymerizable group may be used together. The compound that may be used together with the amide compound according to the invention is preferably a compound having a sulfo group or a salt thereof. The compound may have one or two or more polymerizable groups. However, according to the invention, a compound having one polymerizable group is preferable.

As this compound, a compound represented by Formula (SM) below is preferable.

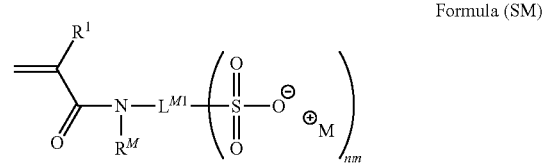

Formula (SM)

In Formula (SM), $R^1$ and $M^+$ have the same meanings as $R^1$ and $M^+$ in Formula (1), and preferable ranges thereof are also the same. nm represents an integer of 1 to 3, and $L^{M1}$ represents an nm+1-valent linking group. $R^M$ represents a hydrogen atom or a substituent.

nm is preferably 1 or 2 and more preferably 1.

$L^{M1}$ is preferably an alkylene group and an arylene group, or a combination thereof.

Among these, $L^{M1}$ is preferably an alkylene group or an arylene group.

The alkylene group is a linear or branched alkylene group, and the number of carbon atoms thereof is preferably 1 to 10, more preferably 1 to 8, even more preferably 1 to 6, and particularly preferably 2 to 5. The alkylene group may have a substituent. As the substituent, an alkyl group or an aryl group is preferable.

The arylene group preferably has 6 to 12 carbon atoms, and may have a substituent.

Hereinafter, specific examples of the compound represented by Formula (SM) are provided, but the invention is not limited thereto.

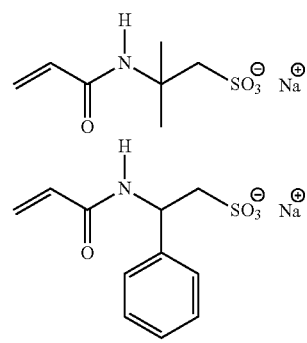

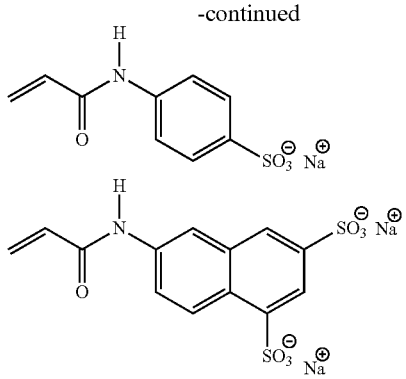

The density of sulfonic acid is preferably 1.5 milliequivalent/g or greater, more preferably 2.0 milliequivalent/g or greater, even more preferably 3.0 milliequivalent/g or greater, and particularly preferably 4.0 milliequivalent/g or greater with respect to the total mass of the compound having a polymerizable group that the curable composition according to the invention contains. The upper limit of the density of sulfonic acid is practically 5.5 milliequivalent/g or less and preferably 5.0 milliequivalent/g or less.

The density of sulfonic acid of the compound represented by Formula (SM) is more preferably 2.0 milliequivalent/g or greater, even more preferably 3.0 milliequivalent/g or greater, and particularly preferably 4.0 milliequivalent/g or greater. The upper limit of the density of sulfonic acid is practically 6.0 milliequivalent/g or less and preferably 5.5 milliequivalent/g or less.

If the density of sulfonic acid with respect to the total mass of the compound having a polymerizable group that the curable composition contains is caused to be in the range described above, it is possible to increase ion (cation) exchange capacity and suppress electrical resistance of the membrane.

The content of the amide compound according to the invention is preferably 10 to 90 parts by mass, more preferably 15 to 70 parts by mass, and particularly preferably 20 to 50 parts by mass with respect to 100 parts by mass of the total solid content of the curable composition.

The content of a compound having a polymerizable group other than the amide compound according to the invention is preferably 30 to 90 parts by mass, more preferably 40 to 90 parts by mass, and particularly preferably 50 to 80 parts by mass with respect to 100 parts by mass of the total solid content of the curable composition.

<Polymerization Initiator>

The curable composition according to the invention is preferably polymerized and hardened in presence of a polymerization initiator and accordingly it is preferable to include a polymerization initiator in the curable composition.

Among the polymerization initiators, according to the invention, a photopolymerization initiator that can allow polymerization with active radiation irradiation is preferable.

Examples of the photopolymerization initiator include aromatic ketones, an acylphosphine compound, an aromatic onium salt compound, organic peroxide, a thio compound, a hexaarylbiimidazole compound, a ketoxime ester compound, a borate compound, an azinium compound, a metallocene compound, an active ester compound, a compound having a carbon halogen bond, and an alkyl amine compound.

The polymerization initiator is not necessarily limited to a photopolymerization initiator, as long as the polymerization initiator can dissolve in respective components or a solvent that is used in the reaction. Examples of the polymerization initiator include an oil soluble peroxide-based thermal polymerization initiator such as benzoyl peroxide (BPO), an oil soluble azo-based thermal polymerization initiator such as azobisisobutyronitrile (AIBN), and a water soluble azo-based thermal polymerization initiator such as azobis cyano valerate (ACVA). In the case where a water ratio in the solvent of the solution polymerization is great, a water soluble peroxide-based thermal polymerization initiator such as ammonium persulfate or potassium persulfate, hydrogen peroxide water, or the like can be used. A redox agent such as ferrocene or amines can be combined.

Preferable examples of aromatic ketones, an acylphosphine oxide compound, and a thio compound include compounds having a benzophenone skeleton or a thioxanthone skeleton disclosed in "RADIATION CURING IN POLYMER SCIENCE AND TECHNOLOGY", pages 77 to 117 (1993). More preferable examples include an α-thiobenzophenone compound disclosed in JP1972-6416B (JP-S47-6416B), a benzoin ether compound disclosed in JP1972-3981B (JP-S47-3981B), an α-substituted benzoin compound disclosed in JP1972-22326B (JP-S47-22326B), a benzoin derivative disclosed in JP1972-23664B (JP-S47-23664B), aroyl phosphonic acid ester disclosed in JP1982-30704A (JP-S57-30704A), dialkoxybenzophenone disclosed in JP1985-26483B (JP-S60-26483B), benzoin ethers disclosed in JP1985-26403B (JP-S60-26403B) and JP1987-81345A (JP-S62-81345A), α-aminobenzophenones disclosed in JP1989-34242B (JP-H01-34242B), U.S. Pat. No. 4,318,791A, and EP0284561A1, p-di(dimethylaminobenzoyl)benzene disclosed in JP1990-211452A (JP-H02-211452A), thio-substituted aromatic ketone disclosed in JP1986-194062A (JP-S61-194062A), acylphosphinesulfide disclosed in JP1990-9597B (JP-H02-9597B), acylphosphine disclosed in JP1990-9596B (JP-H02-9596B), thioxanthones disclosed in JP1988-61950B (JP-S63-61950B), and coumarins disclosed in JP1984-42864B (JP-S59-42864B). Polymerization initiators disclosed in JP2008-105379A and JP2009-114290A are also preferable. Examples thereof include the polymerization initiators disclosed in pages 65 to 148 of "ULTRAVIOLET LIGHT HARDENING SYSTEM" (issued by General Technology Center, 1989) written by KATO Kiyomi.

According to the invention, a water soluble polymerization initiator is preferable.

Here, the fact that the polymerization initiator is water soluble means that 0.1 mass % or greater of the polymerization initiator is dissolved in distilled water at 25° C. The water soluble polymerization initiator is more preferably dissolved by 1 mass % or greater and particularly preferably dissolved by 3 mass % or greater in distilled water at 25° C.

According to the invention, the content of the polymerization initiator is preferably 0.1 to 10 parts by mass, more preferably 0.1 to 5 parts by mass, and even more preferably 0.3 to 2 parts by mass with respect to 100 parts by mass which is the total solid content in the curable composition.

<Polymerization Inhibitor>

It is preferable that the curable composition according to the invention includes a polymerization inhibitor.

As the polymerization inhibitor, an arbitrary polymerization inhibitor can be used. Examples thereof include a phenol compound, a hydroquinone compound, an amine compound, a mercapto compound, and a nitroxyl radical compound.

Specific examples of the phenol compound include a hindered phenol (phenol having a t-butyl group in an ortho position, and representative examples thereof include 2,6-di-t-butyl-4-methylphenol) and bisphenol. Specific examples of the hydroquinone compound include monomethyl ether hydroquinone. Specific examples of the amine compound include N-nitroso-N-phenyl hydroxylamine and N,N-diethylhydroxylamine. Specific examples of the nitroxyl radical compound include 4-hydroxy TEMPO (4-hydroxy-2,2,6,6-tetramethylpiperidine-1-oxyl free radical).

These polymerization inhibitors may be used singly or two or more types thereof may be used in combination.

A content of the polymerization inhibitor is preferably 0.01 to 5 parts by mass, more preferably 0.01 to 1 part by mass, and even more preferably 0.01 to 0.5 parts by mass with respect to 100 parts by mass of the total solid content in the curable composition.

<Solvent>

The curable composition according to the invention may include a solvent. The content of the solvent in the curable composition is preferably 5 to 40 mass %, more preferably 10 to 40 mass %, and even more preferably 20 to 40 mass % with respect to the entire curable composition.

If the solvent is included, the hardening (polymerization) reaction evenly and smoothly proceeds. In the case where the porous support is impregnated with the curable composition, impregnation smoothly proceeds.

As the solvent, water or a mixed liquid of water and a solvent of which solubility in water is 5 mass % or greater is preferable, and a mixed solvent of water and a solvent that is freely mixed with water is more preferable. Therefore, a solvent selected from water and a water soluble solvent is preferable.

As the water soluble solvent, particularly, an alcohol-based solvent, an ether-based solvent which is an aprotic polar solvent, an amide-based solvent, a ketone-based solvent, a sulfoxide-based solvent, a sulfone-based solvent, a nitrile-based solvent, and an organic phosphorus-based solvent are preferable.

Examples of the alcohol-based solvent include methanol, ethanol, isopropanol, n-butanol, ethylene glycol, propylene glycol, diethylene glycol, and dipropylene glycol. These can be used singly or two or more types thereof may be used in combination.

Examples of an aprotic polar solvent include dimethyl sulfoxide, dimethylimidazolidinone, sulfolane, N-methylpyrrolidone, dimethylformamide, acetonitrile, acetone, dioxane, tetramethylurea, hexamethylphosphoramide, hexamethylphosphorotriamide, pyridine, propionitrile, butanone, cyclohexanone, tetrahydrofuran, tetrahydropyran, ethylene glycol diacetate, and γ-butyrolactone as preferable solvents. Among these, dimethyl sulfoxide, N-methylpyrrolidone, dimethylformamide, dimethylimidazolidinone, sulfolane, acetone or acetonitrile, and tetrahydrofuran are preferable. These can be used singly or two or more types thereof may be used in combination.

<<Functional Polymer Hardened Product>>

The functional polymer hardened product according to the invention is manufactured by performing polymerization hardening reaction on the curable composition according to the invention.

The functional polymer hardened product according to the invention has a structure represented by Formula (1-1) below.

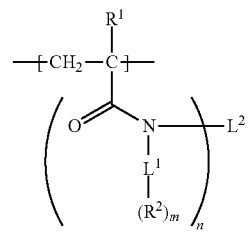

Formula (1-1)

In Formula (1-1), m, n, $R^1$, $R^2$, $L^1$, and $L^2$ have respectively the same meanings as m, n, $R^1$, $R^2$, $L^1$, and $L^2$ in Formula (1), and preferable ranges thereof are also the same.

According to the invention, the structure represented by Formula (1-1) preferably is a structure represented by Formula (2-1) or (3-1) below.

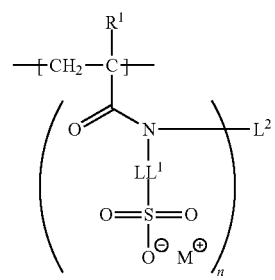

Formula (2-1)

In Formula (2-1), n, $R^1$, $LL^1$, $L^2$, and $M^+$ have respectively the same meanings as n, $R^1$, $LL^1$, $L^2$, and $M^+$ in Formula (2), and preferable ranges thereof are also the same.

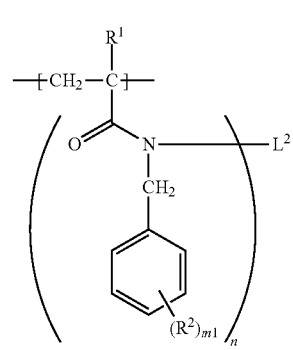

Formula (3-1)

In Formula (3-1), m1, n, $R^1$, $L^2$, and $R^2$ have respectively the same meanings as m1, n, $R^1$, $L^2$, and $R^2$ in Formula (3), and preferable ranges thereof are also the same.

<Support>

In the case where the functional polymer hardened product according to the invention is used as a cation-exchange membrane which is an ion-exchange membrane, the functional polymer hardened product according to the invention may have a support. Hereinafter, descriptions are made by substituting the functional polymer hardened product with an ion-exchange membrane.

In order to provide the ion-exchange membrane having favorable mechanical strength, many technologies can be used. Among these, it is preferable to use a support as a reinforcing material of the membrane, and a porous support is preferable as the support. A portion of the membrane can be formed by coating or impregnating the porous support with the curable composition according to the invention and polymerizing and hardening this curable composition.

Examples of the porous support described above include synthetic woven fabric, synthetic nonwoven fabric, a sponge-shaped film, or a film having fine through holes. Examples of the material for forming the porous support may be a porous membrane based on polyolefin (polyethylene, polypropylene, and the like), polyacrylonitrile, polyvinyl chloride, polyester, polyamide, and copolymers thereof; or porous membranes based on polysulfone, polyether sulfone, polyphenylenesulfone, polyphenylenesulfide, polyimide, polyethermide, polyamide, polyamideimide, polyacrylonitrile, polycarbonate, polyacrylate, cellulose acetate, polypropylene, poly(4-methyl-1-pentene), polyvinylidene fluoride, polytetrafluoroethylene, polyhexafluoropropylene, polychlorotrifluoroethylene, and copolymers thereof. Among these, according to the invention, polyolefin is preferable.

Commercially available porous supports or the commercially available reinforcing materials are, for example, commercially available from Japan Vilene Company, Ltd., Freudenberg Filtration Technologies (Novatexx material), and Sefar AG.

In the case where photopolymerization hardening reaction is performed, it is required that the porous support and the reinforcing material do not block the wavelength range of the irradiation light. Therefore, it is required that the porous support and the reinforcing material transmit light in wavelengths used in the photopolymerization hardening reaction. It is preferable that the curable composition that forms the ion-exchange membrane easily permeates the porous support or the reinforcing material.

It is preferable that the porous support or the reinforcing material has hydrophilicity. In order to impart hydrophilicity to the support, general methods such as a corona treatment, an ozone treatment, a sulfate treatment, and a silane coupling agent treatment can be used.

In the case where the ion-exchange membrane has a support, the thickness of the ion-exchange membrane including the support is preferably 30 to 150 μm, more preferably 60 to 130 μm, and particularly preferably 90 to 110 μm.

<<Characteristics of Ion-Exchange Membrane>>

In a case where the functional polymer hardened product according to the invention is used as the ion-exchange membrane, it is preferable to have characteristics below.

The ion-exchange membrane which is the functional polymer hardened product according to the invention has the ion exchange capacity of preferably 2.0 meq/g or greater, more preferably 2.5 meq/g or greater, and particularly preferably 3.5 meq/g or greater based on the total dry mass of a membrane, an arbitrary porous support that is continuously in contact with the obtained membrane, and an arbitrary porous reinforcing material. The upper limit of the ion exchange capacity is not particularly limited, but is practically 7.0 meq/g or less. Here, meq refers to milliequivalent.

The ion-exchange membrane which is the functional polymer hardened product according to the invention has a charge density of preferably 100 meq/m$^2$ or greater, more preferably 250 meq/m$^2$ or greater, and particularly preferably 300 meq/m$^2$ or greater based on the area of the dry membrane. The upper limit of the charge density is not particularly limited, but is practically 3,500 meq/m$^2$ or less.

The permselectivity with respect to a cation such as Na$^+$ of the ion-exchange membrane (cation-exchange membrane) which is the functional polymer hardened product according to the invention is preferably 0.98 or greater and more preferably 0.99 or greater. As the permselectivity of the ion comes closer to 1.0 which is an ideal value, the permselectivity is more preferable.

The electrical resistance (membrane resistance) of the ion-exchange membrane which is the functional polymer hardened product according to the invention is preferably 2.5 Ω·cm$^2$ or less, more preferably 2.0 Ω·cm$^2$ or less, and particularly preferably 1.5 Ω·cm$^2$ or less. As the electrical resistance is lower, the electrical resistance is more preferable, and the electrical resistance is preferably the lowest value in the realizable scope for exhibiting an effect of the invention.

The swelling ratio (dimensional change rate due to swelling) of the ion-exchange membrane which is the functional polymer hardened product according to the invention in water is preferably less than 30%, more preferably less than 15%, and particularly preferably less than 8%. The swelling ratio can be controlled by selecting a proper parameter in a hardening step.

The electrical resistance, the permselectivity of the ion, and the swelling ratio % in water can be measured by the method disclosed in pages of 319, 217, and 218 of Membrane Science (2008) and pages 193 to 195 of Experimental method in membrane science (1984) written by Nakagaki Masayuki.

The hydraulic permeability of the ion-exchange membrane which is the functional polymer hardened product according to the invention is preferably $5.0 \times 10^{-5}$ ml/m$^2$/Pa/hr or less, more preferably $4.7 \times 10^{-5}$ ml/m$^2$/Pa/hr or less, and particularly preferably $4.4 \times 10^{-5}$ ml/m$^2$/Pa/hr or less.

As a value represented by a product of the membrane resistance (Ω·cm$^2$) and the hydraulic permeability (ml/m$^2$/Pa/hr) is lower, the ion-exchange membrane which is the functional polymer hardened product according to the invention is more preferable. That is, the product of the membrane resistance and the hydraulic permeability is preferably $10.0 \times 10^{-5}$ (Ω·cm$^2$·ml/m$^2$/Pa/hr) or less, more preferably $8.0 \times 10^{-5}$ (Ω·cm$^2$·ml/m$^2$/Pa/hr) or less, and even more preferably $7.0 \times 10^{-5}$ (Ω·cm$^2$·ml/m$^2$/Pa/hr) or less.

A mass average molecular weight of the polymer having a structural unit represented by Formula (1-1) that forms the ion-exchange membrane which is the functional polymer hardened product according to the invention is several hundreds of thousands or higher since three dimensional crosslink is formed, and may not be substantially measured. Generally, the mass average molecular weight is considered unlimited.

<<Method of Manufacturing Functional Polymer Hardened Product>>

The method of manufacturing the functional polymer hardened product according to the invention is described as the method of manufacturing the ion-exchange membrane which is the most preferable use thereof.

The ion-exchange membrane which is the functional polymer hardened product according to the invention can be prepared in a batch type by fixing a support, but the membrane can be prepared in a continuous type by moving a support. The support may be a roll shape that is continuously rewound. In the case where the membrane is prepared in the continuous method, steps of loading the support on a belt that continuously moves, continuously applying, polymerizing, and hardening the coating liquid which is the curable composition for forming the ion-exchange membrane, and forming the membrane can be continuously performed. Here, any one of the applying step and the membrane forming step may be continuously performed.

Independently from the support, the curable composition for forming the ion-exchange membrane is impregnated in the porous support, and a temporary support (after the polymerization hardening reaction is completed, the membrane is peeled from the temporary support) may be used until the polymerization hardening reaction is completed.

This temporary support is not particularly limited, as long as there is no need to consider material penetration, and the temporary support includes, for example, a metal plate such as a polyethylene terephthalate (PET) film or an aluminum plate and can be fixed for forming the membrane.

Polymerizing and hardening can be performed without using a support other than the porous support, by impregnating the curable composition for forming the ion-exchange membrane in the porous support exchange membrane.

The porous support can be coated or impregnated with the curable composition for forming the ion-exchange membrane by various methods, for example, curtain coating, extrusion coating, air-knife coating, slide coating, nip roller coating, forward roll coating, reverse roll coating, impregnation coating, kiss coating, rod bar coating, or spray coating. In a case where plural layers are coated, simultaneous multilayer coating can be performed. In order to perform simultaneous multilayer coating, curtain coating, slide coating, slot die coating, and extrusion coating are preferable.

In a case where the ion-exchange membrane is manufactured in the continuous method, the ion-exchange membrane is preferably manufactured by a manufacturing unit at least including a composition applying unit that continuously apply a curable composition that forms an ion-exchange membrane while moving the support and more preferably manufactured by a manufacturing unit including a composition applying unit, an irradiation source for hardening the composition, a membrane collecting portion, and means for transferring the support from the composition applying unit to the irradiation source or the membrane collecting portion.

In this manufacturing example, the ion-exchange membrane is manufactured by steps of (i) applying or impregnating the curable composition for forming the ion-exchange membrane that is the functional polymer hardened product according to the invention on the support (preferably the porous support), (ii) performing polymerization hardening reaction on the curable composition by active radiation irradiation or heating, and (iii) removing the membrane formed as desired from the support.

In (ii), the heating may be performed in combination with active radiation irradiation. In the step (i), it is preferable that the curable composition is impregnated in the support.

[Active Radiation Irradiation]

If the ion-exchange membrane is manufactured in a step order of coating (or impregnating), photoirradiation, and multilayer collection, with respect to the arrangement of this equipment, the composition applying unit (or impregnating unit) is positioned at an upper stream position than the irradiation source, and thus the irradiation source is disposed at an upper stream position than a multilayer collecting portion.

In order to cause the curable composition to have a sufficient fluidity for application with a high speed applicator, the viscosity of the curable composition for forming the ion-exchange membrane at 35° C. is preferably less than 4,000 mPa·s, more preferably 1 to 1,000 mPa·s, and most preferably 1 to 500 mPa·s. In the case of slide bead coating, the viscosity at 35° C. is preferably 1 to 100 mPa·s.

In the high speed applicator, the transferred support can be coated with the coating liquid which is the curable composition for forming the ion-exchange membrane at a speed of greater than 15 m/min, and also can be applied at a speed of greater than 400 m/min.

Particularly, in the case where the support is used in order to enhance the mechanical strength, before the surface of the support is coated with the curable composition according to the invention, this support may be subjected to a corona discharge treatment, a glow discharge treatment, a flame treatment, an ultraviolet irradiation treatment, and the like, for example, in order to improve the wettability and adhesion force of the support.

The polymerizing and hardening of the curable composition for forming the ion-exchange membrane starts preferably within 60 seconds, more preferably within 15 seconds, particularly preferably within 5 seconds, and most preferably within 3 seconds, from application or impregnation of the curable composition to the support.

The active radiation irradiation time of the polymerizing and hardening is preferably less than 10 seconds, more preferably less than 5 seconds, particularly preferably less than 3 seconds, and most preferably less than 2 seconds. In the continuous method, the irradiation is performed continuously, and polymerization hardening reaction time is determined considering the speed of the curable composition moving through the irradiation beam.

In the case where ultraviolet light (UV light) having high strength is used in the polymerization hardening reaction, a considerable amount of heat is generated, and thus it is preferable to cool at least one (preferably all) of a lamp of the light source, the porous support, or the formed membrane with the air for cooling or the like, in order to prevent the overheat. In the case of irradiation with the considerable light amount of infrared light (IR light) together with UV beams, the irradiation is performed with UV light by using an IR reflective quartz plate as a filter.

The active radiation is preferably ultraviolet rays. The irradiation wavelength is preferably a wavelength that allows absorption of a polymerization initiator included in a composition. Therefore, the irradiation wavelength is preferably a wavelength that is the same as the absorption wavelength of the polymerization initiator or a wavelength that is overlapped with the absorption wavelength. Examples thereof include UV-A (400 to 320 nm), UV-B (320 to 280 nm), and UV-C (280 to 200 nm).

The ultraviolet light source is a mercury arc lamp, a carbon arc lamp, a low pressure mercury lamp, a medium pressure mercury lamp, a high pressure mercury lamp, a swirl-flow plasma arc lamp, a metal halide lamp, a xenon lamp, a tungsten lamp, a halogen lamp, laser, and an ultraviolet light emitting diode. As the ultraviolet light source, ultraviolet light emitting lamps of the medium or high pressure mercury vapor type is particularly preferable. In order to modify an emission spectrum of the lamp, an additive such as metal halide may be additionally provided to a lamp. A lamp having maximum light emission in 200 to 450 nm is particularly appropriate.

The energy output of the irradiation source is preferably from 20 to 1,000 W/cm and more preferably from 40 to 500 W/cm. However, if the desired exposure dose can be realized, the energy output can be higher or lower than the range above. The polymerization hardening of a membrane is adjusted according to the exposure intensity. The exposure dose is measured by High Energy UV Radiometer (UV Power Puck™ manufactured by EIT-Instrument Markets) in the UV-A range indicated in this device, and is preferably 40 mJ/cm² or greater, more preferably 100 to 2,000 mJ/cm², and most preferably 150 to 1,500 mJ/cm². The exposure time can be freely chosen, but is preferably shorter and most preferably less than 2 seconds.

In the case where the high speed coating is performed, plural light sources may be used in order to reach a desired dose. Exposure intensity of these light sources may be equal to or different from each other.

[Polymerizing and Hardening by Heating]

With respect to the ion-exchange membrane that is the functional polymer hardened product according to the invention, even if the membrane is formed by thermal polymerizing and hardening, a membrane exhibiting almost the same performances can be obtained. In this thermal polymerizing and hardening, the heating temperature is preferably 40° C. to 200° C., more preferably 60° C. to 180° C., and particularly preferably 70° C. to 150° C. The heating time is preferably 5 minutes to 12 hours, more preferably 10 minutes to 10 hours, and particularly preferably 10 minutes to 8 hours.

<<Use of Functional Polymer Hardened Product>>

The functional polymer hardened product according to the invention mainly is intended to be used in the ion exchange. However, the membrane of the functional polymer hardened product according to the invention is not limited to the ion exchange, and is considered to be able to be appropriately used also in forward osmosis, reverse osmosis, and the gas separation.

The functional polymer hardened product according to the invention is useful as the ion-exchange membrane, particularly, as the cation-exchange membrane, and can be used in proton conduction, electrodeionization, continuous electrodeionization, electrodialysis, polarity conversion method electrodialysis, and reverse electrodialysis, or devices thereof. The functional polymer hardened product according to the invention can be used not only for general usage but also for a solid polymer electrolyte-type fuel cell. The functional polymer hardened product according to the invention also can be used for a polymer electrolyte and a water-absorbing resin.

An aspect of using the membrane of the functional polymer hardened product according to the invention is not particularly limited, but a single membrane or a stack of the membranes of the functional polymer hardened product can be used in a device such as devices used for the usage described above.

Here, the "stack" refers to a module in which anion-exchange membranes and cation-exchange membranes are alternatively disposed between a pair of electrodes.

EXAMPLES

Hereinafter, the invention is described in more detail with reference to examples, but the invention is not limited to these examples. Unless described otherwise, "part(s)" and "percent (%)" are on a mass basis.

<Synthesis of Amide Compound>

<Synthesis Example 1> Synthesis of Amide Compound (M-1)

An amide compound (M-1) was synthesized in a synthesis scheme below.

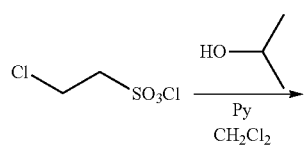

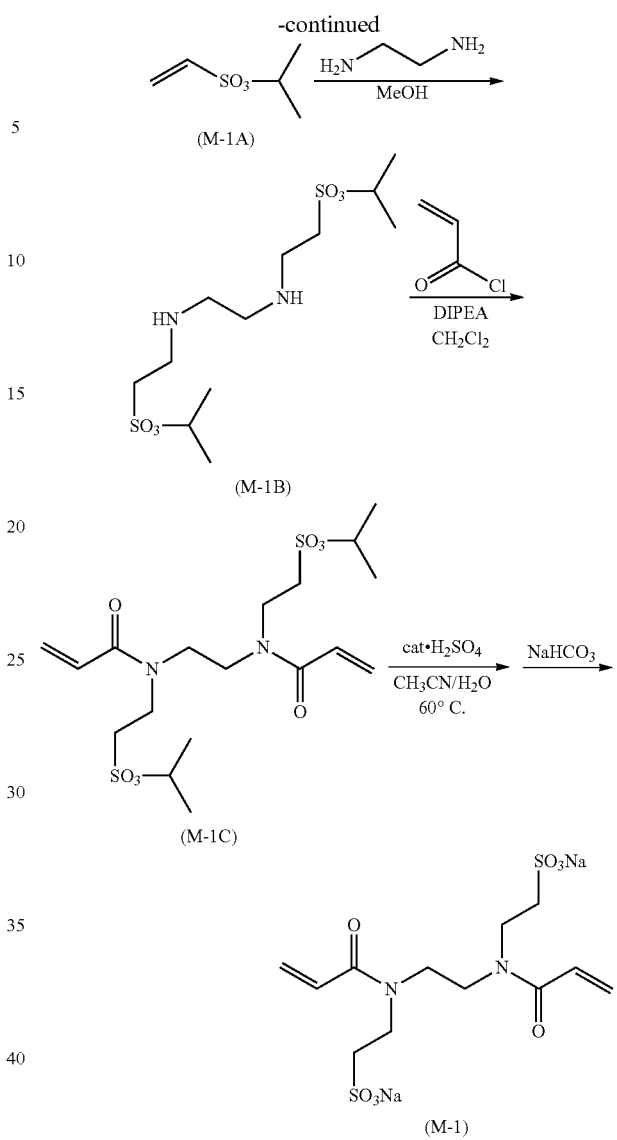

A compound (M-1A) was synthesized by a method disclosed in J. Am. Chem. Soc., 2000, 122, 3375-3385. Subsequently, a mixed solution of 136.7 g of the compound (M-1A) (0.91 mol) and 273.3 g of methanol were added to a mixed solution of 27.4 g of ethylenediamine (0.70 mol, manufactured by Wako Pure Chemical Industries, Ltd.) and 427.7 g of methanol in a reaction system, under ice cooling and were stirred for one hour. The reaction solution was concentrated so as to obtain 164.0 g of a compound (M-1B) (yield: 100%).

86.5 g of acrylic acid chloride (0.96 mol, manufactured by Wako Pure Chemical Industries, Ltd.) was added to a mixed solution of 164.0 g of a compound (M-1B) (0.46 mol), 123.5 g of diisopropylethylamine (0.96 mol, manufactured by Wako Pure Chemical Industries, Ltd.), and 3,154.3 g of dichloromethane under ice cooling and was stirred for three hours at room temperature (25° C.). The reaction solution was washed with 500.0 mL of water and was concentrated with an evaporator, and the concentrated product was purified with silica gel chromatography, so as to obtain 107.2 g of a compound (M-1C) (yield: 51%).

A mixed solution of 60.1 g of a compound (M-1C) (0.13 mol), 60.1 mg of 4-hydroxy-2,2,6,6-tetramethylpiperidine- 1-oxyl free radicals (0.35 mmol, manufactured by Tokyo Chemical Industry Co., Ltd.), 282.8 mL of acetonitrile, 141.4 mL of water, and 1.3 g of sulfuric acid (0.013 mol) were stirred for five hours at 60° C., pH was adjusted to pH 7 with sodium hydrogen carbonate at room temperature (25° C.), and filtration was performed. Since the filtrated solution was separated into two layers, only an underlayer (aqueous layer) was extracted and left alone for one night (12 hours) under ice cooling, and precipitates were removed by filtration. 1,800 g of ethanol was added, generated crystals were filtrated, blast drying was performed at 40° C. for 10 hours, and 37.5 g of an amide compound (M-1) was obtained as white crystals (yield: 68%).

A structure of the obtained amide compound (M-1) was confirmed with a ¹H-NMR spectrum.

¹H-NMR (DMSO-d6, 300 MHz) δ: 2.59-2.79 (4H), 3.29-3.69 (8H), 5.56-5.72 (2H), 6.00-6.19 (2H), and 6.51-6.81 (2H)

<Synthesis Example 2> Synthesis of Amide Compound (M-2)

An amide compound (M-2) was synthesized in the same manner as in Synthesis Example 1 by changing ethylenediamine to meta-xylenediamine.

(M-2)

<Synthesis Example 3> Synthesis of Amide Compound (M-3)

An amide compound (M-3) was synthesized in a synthesis scheme below.

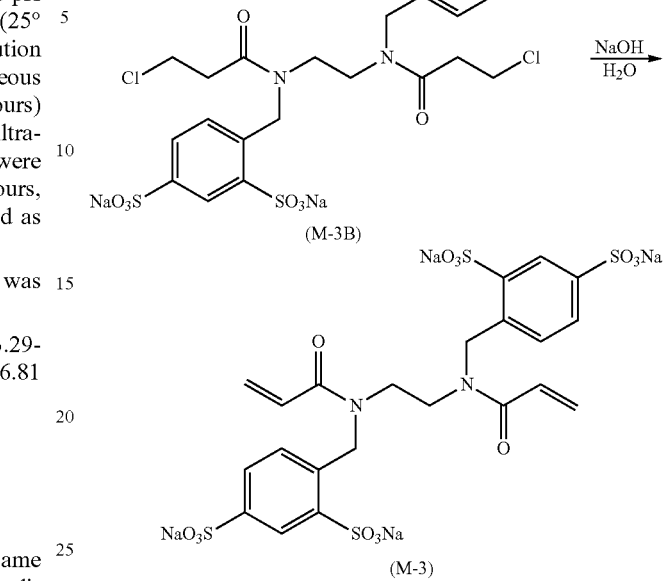

42.1 g of ethylenediamine (0.700 mol, manufactured by Wako Pure Chemical Industries, Ltd.) was added to a mixed solvent of 467 g of benzaldehyde-2,4-disulfonic acid disodium (1.51 mol, manufactured by Wako Pure Chemical Industries, Ltd.) and 2,170 g of methanol and was stirred for five hours at 40° C. Subsequently, 53.0 g of sodium borohydride (1.40 mol, manufactured by Wako Pure Chemical Industries, Ltd.) was added and stirred for three hours at room temperature (25° C.). Subsequently, 11.8 L of acetone was added, generated crystals were filtrated, blast drying was performed at 40° C. for 10 hours, so as to obtain 441 g of a compound (M-3A) as pale yellow crystals (yield: 97%).

160 g of 3-chloropropionyl chloride (1.26 mol, manufactured by Wako Pure Chemical Industries, Ltd.) was added to a mixed solution of 389 g of the compound (M-3A) (0.6 mol), 1,650 g of water, and 222 g of sodium hydrogen carbonate (1.32 mol, manufactured by Wako Pure Chemical Industries, Ltd.) under ice cooling and was stirred for three hours.

Subsequently, 25 L of ethanol was added, generated crystals were filtrated, and 525 g of crude crystals of a compound (M-3B) were obtained as pale yellow crystals.

1,000 g of sodium hydroxide 5% aqueous solution was added to 525 g of crude crystals of the compound (M-3B) under ice cooling and was stirred for one hour at room temperature (25° C.). Subsequently, 20 L of ethanol was added, generated crystals were filtrated, blast drying was performed at 40° C. for 10 hours, so as to obtain 185 g of an amide compound (M-3) as pale yellow crystals (yield: 36%).

A structure of the obtained amide compound (M-3) was confirmed with a ¹H-NMR spectrum.

¹H-NMR (DMSO-d6, 300 MHz) δ: 2.73 (2H), 5.14-5.39 (2H), 5.63-5.85 (2H), 6.07-6.19 (2H), 6.31-6.83 (2H), 7.31 (4H), 7.81 (2H), and 8.20 (2H)

<Synthesis Example 4> Synthesis of Amide Compound (M-4)

An amide compound (M-4) was synthesized in the same manner as in Synthesis Example 3 by changing ethylenediamine to meta-xylenediamine.

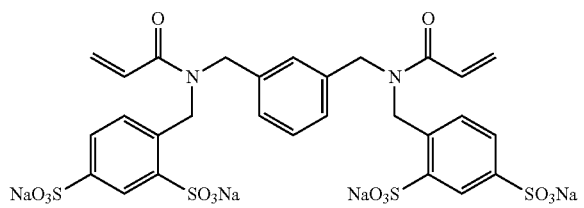
(M-4)

Amide compounds (M-5) to (M-7) presented in Table 1 below were compounds below disclosed in JP2005-514338A.

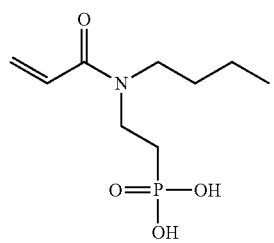
(M-5)

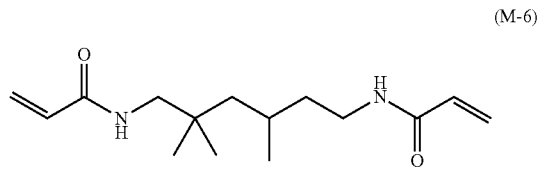
(M-6)

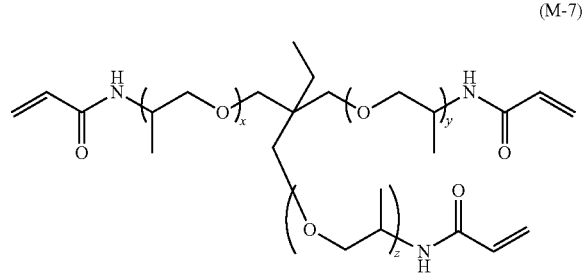
(M-7)

In Table 1 below, amide compounds (M-1) to (M-7) and BAMPS described below were used as crosslinking agents for convenience and AMPS described below was classified as a monofunctional monomer.

Example 1

(Manufacturing of Cation-Exchange Membrane)

An aluminum plate was manually coated with a coating liquid consisting of a composition (unit: g) in the composition of Table 1 below at a speed of about 5 m/min, by using a rod obtained by winding a wire of 150 μm, and subsequently a nonwoven fiber (manufactured by Freudenberg Group, FO-2226-14, thickness: 100 μm) was impregnated with the coating liquid. The remaining coating liquid was removed by using a rod to which a wire was not wound. The temperature of the coating liquid at the time of application was about 50° C. The coating liquid impregnated support obtained above was exposed for 0.47 seconds by using an UV exposure machine (manufactured by Fusion UV Systems, model type: Light Hammer LH6, D-bulb, speed: 15 m/min, 100% intensity), and polymerization hardening reaction was performed for the polymerizing and hardening time of 0.8 seconds, so as to prepare a cation-exchange membrane. The obtained membrane was removed from the aluminum plate and was preserved for at least 12 hours in a 0.1 M NaCl aqueous solution at room temperature (25° C.), so as to manufacture the cation-exchange membrane.

Examples 2 to 4 and Comparative Examples 1 and 2

Cation-exchange membranes of Examples 2 to 4 and Comparative Examples 1 and 2 were respectively manufactured in the same manner as Example 1 except for changing compositions to compositions presented in Table 1 below, in the manufacturing of the cation-exchange membrane in Example 1.

With respect to the cation-exchange membranes manufactured in Examples 1 to 4 and Comparative Examples 1 and 2, items below were evaluated.

[Density of Sulfonic Acid (milliequivalent/g)]

The measuring of the amount of the sulfonic acid group of the cation-exchange membrane was performed in the method below.

The cation-exchange membrane was immersed in a 1.0 M hydrochloric acid aqueous solution at room temperature (25° C.) for 24 hours, such that an acid type ($H^+$ type) was completely formed. Thereafter, the cation-exchange membrane was immersed in pure water for 24 hours at room temperature (25° C.), free ions in the cation-exchange membrane were washed, the cation-exchange membrane was immersed in a 3.0 M NaCl aqueous solution, at room temperature (25° C.) for 24 hours, so as to form a sodium type ($Na^+$ type), and substituted $H^+$ was neutralized and titrated in a 0.02 M NaOH aqueous solution, so as to obtain the amount of the sulfonic acid group. An amount of the phosphonic acid was obtained in the same manner. A density of sulfonic acid and a density of phosphonic acid were respectively calculated from the amount of the sulfonic acid group, the amount of the phosphonic acid group, numbers of sulfonic acid groups or phosphonic acid groups per one molecule of a monofunctional monomer or a crosslinking agent, and a mass of a membrane.

[Permselectivity]

The permselectivity was calculated by measuring a membrane potential (V) by static membrane potential measuring. Two cells (electrolytic bath) were separated by the membrane of a measurement target. Before the measurement, the membrane was brought into equilibrium for about 16 hours in the 0.05 M NaCl aqueous solution at room temperature (25° C.). Thereafter, NaCl aqueous solutions having different concentrations were respectively poured into electrolytic baths on the opposite sides of the membrane of the measurement target.

100 mL of a 0.05 M NaCl aqueous solution was poured to one cell. 100 mL of an 0.5 M NaCl aqueous solution was poured to the other cell.

After the temperature of the NaCl aqueous solution in the cells was stably maintained to 25° C. in a thermostatic water tank, while the both solutions were caused to flow toward the membrane surface, the both electrolytic bath and Ag/AgCl reference electrodes (manufactured by Metrohm AG) were connected with salt bridges, membrane potentials (V) were measured, and permselectivity t was calculated by Equation (a) below.

The effective area of the membrane was 1 cm².

$$t = (a+b)/2b \qquad \text{Equation (a)}$$

Respective reference numerals in Equation (a) denote as follows.

a: membrane potential (V)
b: 0.5915 log($f_1 c_1/f_2 c_2$) (V)
$f_1$ and $f_2$: NaCl activity coefficients of both cells
$c_1$ and $c_2$: NaCl concentrations (M) of both cells

[Electric Resistance (Ω·cm²) of Membrane]

Both sides of the membrane immersed in a 0.5 M NaCl aqueous solution for two hours at room temperature (25° C.) were wiped off with a dry filter paper, and were put into a two-chamber-type cell (effective membrane area: 1 cm², Ag/AgCl reference electrodes (manufactured by Metrohm AG) as electrodes). Both chambers were filled with 100 mL of the NaCl aqueous solution having the same concentration, and the cell was placed in a thermostatic water tank at 25° C. and was left alone until the cell reached equilibrium. A liquid temperature in the cell exactly reached 25° C., and then electric resistance $r_1$ was measured using an alternative current bridge (frequency: 1,000 Hz). The concentration of the NaCl aqueous solution for measurement was adjusted to 0.5 M. Next, the membrane was removed, and electric resistance $r_2$ between both electrodes was measured only with a 0.5 M NaCl aqueous solution to obtain electric resistance r of the membrane as $r_1 - r_2$.

In Table 1 below, the "electric resistance of membrane" was simply referred to as "membrane resistance".

[Hydraulic Permeability (ml/m²/Pa/hr)]

Hydraulic permeability of the membrane was measured using a device having a flow channel 10 shown in FIG. 1. In FIG. 1, reference numeral 1 represents a membrane, and reference numerals 3 and 4 represent flow channels of a feed solution (pure water) and a draw solution (3 M NaCl aqueous solution), respectively. An arrow of reference numeral 2 shows a flow of water separated from the feed solution.

400 mL of feed solution and 400 mL of draw solution were brought into contact (membrane contact area of 18 cm²) through the membrane, and each solution was allowed to flow at a flow rate of 0.11 cm/sec in a direction of an arrow of a reference numeral 5 using a Perista pump. A rate at which water in the feed solution permeates into the draw solution through the membrane was analyzed by measuring masses of the feed solution and the draw solution on a real time basis so as to obtain the hydraulic permeability.

In Table 1, evaluation was performed with values of (electrical resistance of membrane×hydraulic permeability). Here, it is preferable that the electrical resistance of the membrane was low and the hydraulic permeability was also low. As a result, it is preferable that the value of the (electrical resistance of membrane×hydraulic permeability) is low.

[Pin Hole Test]

The membrane for measuring was coated with Pt having the thickness of 1.5 nm and the number of pin holes was examined by using a scanning electron microscope (SEM).

(Measurement Condition)
Acceleration voltage: 2 kV
Working distance: 4 mm
Aperture diaphragm: 4
Magnification: ×100,000 times
Inclination of field of view: 3°

Evaluation of pin holes was carried out from an SEM picture, in view of the following.

(Evaluation Criteria)
A: A defect or a pin hole was not observed.
B: 1 to 2 of defects or pin holes were observed.
C: 3 or more of defects or pin holes were observed.

[Membrane Mass Decreasing Rate (%) After Ultrasonic Treatment]

300 mL of ion exchange water was poured to a 500 mL glass beaker, and the cation-exchange membranes manufactured in Examples 1 to 4, and Comparative Examples 1 and 2 were immersed in this ion exchange water. An ultrasonic treatment was further performed in a table-type ultrasonic Cleaner 1510 manufactured by Branson Ultrasonics Corporation at 25° C. for 60 minutes. The membrane masses were measured before and after the ultrasonic treatment, and the membrane mass decreasing rates were calculated based on the expression below, so as to evaluate stability of the cation-exchange membrane.

(Membrane mass before ultrasonic treatment−membrane mass after ultrasonic treatment)/membrane mass before ultrasonic treatment×100

[pH Resistance]

The membranes were respectively immersed in a hydrochloric acid aqueous solution of pH 1 and a sodium hydroxide aqueous solution of pH 14 and were preserved at 40° C. for three hours. The rate (retention rate (%)) of the hydraulic permeability of the membrane after immersion to the hydraulic permeability of the membranes before immersion was calculated.

In all of the hydrochloric acid aqueous solution of pH 1 and the sodium hydroxide aqueous solution of pH 14, a case where the retention rate of the hydraulic permeability of the membrane before and after the immersion was 90% or greater was evaluated as "A", and a case where the retention rate of the membrane in any one of the solutions was less than 90% was evaluated as "C".

The obtained results were summarized and presented in Table 1.

Abbreviations of compounds presented in Table 1 represent compounds below.

AMPS: 2-acrylamide-2-methylpropane sulfonic acid sodium 50 wt % aqueous solution (manufactured by Sigma-Aldrich Co., LLC.) (Values in Table 1 are values expressed in terms of solid contents)

BAMPS: Compound below disclosed in U.S. Pat. No. 4,034,001A

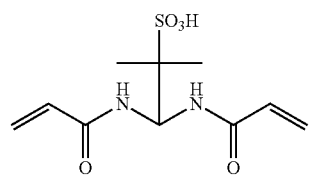 [SMILES: C=CC(=O)NC(NC(=O)C=C)C(C)(C)S(=O)(=O)O]

MEHQ: Monomethyl ether hydroquinone
Darocur (Registered trademark) 1173: product name, manufactured by BASF Japan Ltd.
Irgacure (Registered trademark) 2959: product name, manufactured by BASF Japan Ltd.

Here, with respect to Table 1 below, the expression "-" means not being included.

TABLE 1

| Item | Type | Molecular weight | Number of sulfonic acid groups or phosphonic acid groups | Density of sulfonic acid or phosphonic acid (milliequivalent/g) | Example 1 | Example 2 | Example 3 | Example 4 | Comparative Example 1 | Comparative Example 2 |
|---|---|---|---|---|---|---|---|---|---|---|
| Monofunctional monomer | AMPS | 229.23 | 1 | 4.36 | 70 | 70 | 70 | 70 | — | 57 |
| Crosslinking agent | M-1 | 428.39 | 2 | 4.67 | 30 | — | — | — | — | — |
| | M-2 | 504.49 | 2 | 3.96 | — | 30 | — | — | — | — |
| | M-3 | 756.62 | 4 | 5.29 | — | — | 30 | — | — | — |
| | M-4 | 832.71 | 4 | 4.80 | — | — | — | 30 | — | — |
| | M-5 | 266.38 | 1 | 3.75 | — | — | — | — | 29 | — |
| | BAMPS | 276.31 | 1 | 3.62 | — | — | — | — | — | 43 |
| | M-6 | 266.38 | — | 0 | — | — | — | — | 29 | — |
| | M-7 | — | — | 0 | — | — | — | — | 42 | — |
| Polymerization inhibitor | MEHQ | — | — | — | 0.1 | 0.1 | 0.1 | 0.1 | 0.1 | 0.1 |
| Polymerization initiator | Darocur 1173 | — | — | — | 1 | 1 | 1 | 1 | 1 | 1 |
| | Irgacure 2959 | — | — | — | 1 | 1 | 1 | 1 | 1 | 1 |
| Solvent | Pure water | — | — | — | 55 | 55 | 55 | 55 | 55 | 55 |
| Density of sulfonic acid | Density of sulfonic acid (milliequivalent/g) | — | — | — | 4.45 | 4.24 | 4.64 | 4.49 | 1.07 | 3.93 |
| Evaluation items | Permselectivity | — | — | — | 1 | 1 | 1 | 1 | 0.98 | 0.97 |
| | Membrane resistance ($\Omega \cdot cm^2$) | — | — | — | 1.5 | 1.6 | 1.4 | 1.5 | 3.5 | 1.8 |
| | Hydraulic permeability ($\times 10^{-5}$ ml/m$^2$/Pa/hr) | — | — | — | 4.1 | 4.1 | 4.8 | 4.9 | 5.5 | 12.5 |
| | (Membrane resistance) × (Hydraulic permeability) × $10^{-5}$ ($\Omega \cdot cm^2 \cdot$ ml/m$^2$/Pa/hr) | — | — | — | 6 | 7 | 7 | 7 | 19 | 23 |
| | Pin hole test | — | — | — | A | A | A | A | B | B |
| | Membrane mass decreasing rate (%) after ultrasonic treatment | — | — | — | 0.1 | 0.1 | 0.1 | 0.2 | 0.7 | 1.4 |
| | pH resistance | — | — | — | A | A | A | A | A | C |

As clearly understood from Table 1, the cation-exchange membranes (Examples 1 to 4) of which has a density of sulfonic acid according to the invention is 4 mmol/g or greater and which were manufactured from curable compositions including the amide compound represented by Formula (1) all realized high permselectivity, low membrane resistance, and low hydraulic permeability. With respect to the cation-exchange membranes according to the invention, all products of the electrical resistance of the membrane and the hydraulic permeability represent low values, and thus it was possible to know that the cation-exchange membranes according to the invention were cation-exchange membranes having excellent durability and high performances.

In contrast, in Comparative Example 1, it was understood that further improvements on the electrical resistance of the membrane and the hydraulic permeability were required. In Comparative Example 2, it was understood that further improvements on hydraulic permeability and durability were required.

The invention was described in detail with reference to embodiments thereof, unless described otherwise, any details of the description according to the invention are not intended to limit the invention, and it is obvious that the invention is broadly construed without departing from the spirit and the scope of the invention described in the accompanying claims.

EXPLANATION OF REFERENCES

1 membrane
2 arrow indicating that water in the feed solution permeates into the draw solution through the membrane
3 flow channel of feed solution
4 flow channel of draw solution
5 flowing direction of liquid
10 flow channel of hydraulic permeability determination device

What is claimed is:
1. A curable composition comprising:
    an amide compound that is represented by Formula (1) below and of which a density of sulfonic acid is 3.9 milliequivalent/g or greater,

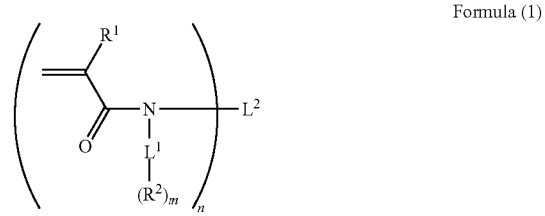

Formula (1)

in Formula (1), m represents an integer of 1 or greater; n represents an integer of 2 or greater; $L^1$ represents a m+1-valent linking group; $L^2$ represents an n-valent linking group; $R^1$ represents a hydrogen atom or an alkyl group; $R^2$ represents $-SO_3^-M^+$ or $-SO_3R^3$; in a case where there are plural $R^2$'s, not all of the $R^2$'s are $-SO_3R^3$; $M^+$ represents a hydrogen ion, an inorganic ion, or an organic ion; and $R^3$ represents an alkyl group or an aryl group.

2. The curable composition according to claim 1, that is used for forming a functional polymer membrane.

3. The curable composition according to claim 1, that is used for forming an ion-exchange membrane.

4. The curable composition according to claim 1, wherein the amide compound is an amide compound represented by Formula (2) below,

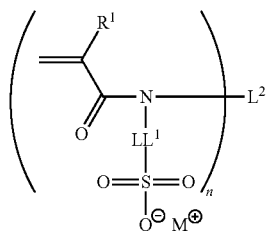

Formula (2)

in Formula (2), $LL^1$ represents an alkylene group; and n, $R^1$, $L^2$, and $M^+$ respectively have the same meanings as n, $R^1$, $L^2$, and $M^+$ in Formula (1).

5. The curable composition according to claim 1, wherein the amide compound is an amide compound represented by Formula (3) below,

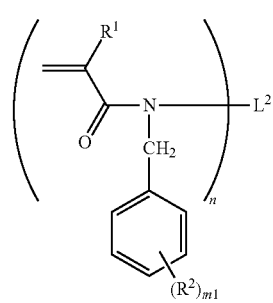

Formula (3)

in Formula (3), m1 represents an integer of 1 to 5; and n, $R^1$, $R^2$, and $L^2$ respectively have the same meanings as n, $R^1$, $R^2$, and $L^2$ in Formula (1).

6. The curable composition according to claim 1, wherein a molecular weight of the amide compound is 900 or less.

7. The curable composition according to claim 1, further comprising:
a polymerization initiator.

8. The curable composition according to claim 1, further comprising:
a solvent.

* * * * *